(12) United States Patent
Shirakawa et al.

(10) Patent No.: US 8,354,113 B2
(45) Date of Patent: Jan. 15, 2013

(54) GENE EXPRESSING A BIFIDOBACTERIUM SURFACE-PRESENTED FUSION PROTEIN

(75) Inventors: Toshiro Shirakawa, Hyogo (JP); Sakura Yamamoto, Hyogo (JP); Takane Katayama, Ishikawa (JP); Jun Wada, Shiga (JP); Yasunobu Kano, Kyoto (JP); Masanori Asada, Osaka (JP); Kosuke Shimamoto, Osaka (JP)

(73) Assignee: Morishita Jintan Co., Ltd., Osaka (JP)

( * ) Notice: Subject to any disclaimer, the term of this patent is extended or adjusted under 35 U.S.C. 154(b) by 0 days.

(21) Appl. No.: 13/124,178

(22) PCT Filed: Sep. 17, 2010

(86) PCT No.: PCT/JP2010/066242
§ 371 (c)(1),
(2), (4) Date: Apr. 14, 2011

(87) PCT Pub. No.: WO2011/034181
PCT Pub. Date: Mar. 24, 2011

(65) Prior Publication Data
US 2012/0177687 A1 Jul. 12, 2012

(30) Foreign Application Priority Data

Sep. 17, 2009 (JP) ................................. 2009-216256
Apr. 22, 2010 (JP) ................................. 2010-099218

(51) Int. Cl.
| | |
|---|---|
| *A61K 39/02* | (2006.01) |
| *A61K 39/145* | (2006.01) |
| *A61K 39/112* | (2006.01) |
| *A61K 39/00* | (2006.01) |
| *A01N 63/00* | (2006.01) |
| *C12N 15/74* | (2006.01) |
| *C07H 21/04* | (2006.01) |

(52) U.S. Cl. ............... 424/200.1; 424/258.1; 424/234.1; 424/209.1; 424/93.4; 424/184.1; 536/23.7; 536/23.72; 435/476

(58) Field of Classification Search ........................ None
See application file for complete search history.

(56) References Cited

U.S. PATENT DOCUMENTS

| | | | |
|---|---|---|---|
| 5,478,570 A | 12/1995 | Sunohara et al. | |
| 7,553,636 B2 | 6/2009 | Sung et al. | |
| 7,740,835 B2 | 6/2010 | Fujimori et al. | |

FOREIGN PATENT DOCUMENTS

| | | |
|---|---|---|
| JP | 62-1288 | 1/1987 |
| JP | 2999535 | 11/1999 |
| WO | 2008/114889 | 9/2008 |

OTHER PUBLICATIONS

Takata et al. J. Gene Medicine 8: 1341-1346, 2006.*
Wada, J. et al., Purification, crystallization and preliminary X-ray analysis of the galacto-N-biose-/lacto-N-biosel-I-binding protein (GL-BP) of the ABC transporter from *Bifidobacterium longum* JCM1217. Acta Crystallogr. Sect. F Struct. Biol. Cryst. Commun., 2007, vol. 63, No. 9, pp. 751-753.
Suzuki, R. et al., Structural and thermodynamic analysis of solute-binding protein from *Bifidobacterium longum* specific for core 1 disaccharide and lacto-N-biose I. J. Biol, Chem., 2008, vol. 283, No. 19, pp. 13165-13173.
Fischetti, V.A. et al., Expression of foreign proteins on gram-positive commensal bacteria for mucosal vaccine delivery. Curro Opin. Biotechnol., 1993, vol. 4, No. 5, pp. 603-610.
PCT/JP2010/066242; International Search Report dated Oct. 21, 2010.
McClelland M. et al., Complete genome sequence of *Salmonella enterica* serovar Typhimurium LT2, Nature, 2001, vol. 413, p. 852-856.
Heidelberg et al., DNA sequence of both chromosomes of the cholera pathogen *Vibrio cholerae*, Nature, 2000, vol. 406, p. 477-484.
Tominaga A. et al., Characterization of cryptic flagellin genes in *Shigella boydii* and *Shigella dysenteriae*, Genes Genet. Syst., 2001, vol. 76, p. 111-120.
Matsumura H. et al., Construction of *Escherichia coli-Bifidobacterium longum* Shuttle Vector Transforming *B. longum* 105-A and 108-A, Biosci. Biotech. Biochem., 1997, vol. 61, pp. 1211-1212.

* cited by examiner

*Primary Examiner* — S. Devi
(74) *Attorney, Agent, or Firm* — Renner, Otto, Boisselle & Sklar, LLP

(57) ABSTRACT

According to the present invention, there is provided a means of expressing and displaying a protein on the cell surface of a *bifidobacterium*. In the gene for expressing a protein on the surface of a *bifidobacterium* of the present invention, a gene coding for a *bifidobacterium*-derived GNB/LNB substrate-binding membrane protein and a gene coding for the target protein or peptide are linked in this order from the 5' end side. Thus, a *bifidobacterium* transformed by introducing the gene for expressing a protein on the surface of a *bifidobacterium* of the present invention expresses the target protein or peptide on the surface thereof. When the target protein or peptide is an antigen protein or an antigen peptide, the transformed *bifidobacterium* of the present invention is useful as an oral vaccine.

21 Claims, 7 Drawing Sheets

P.C.    Positive control (salmonella bacteria-derived flagellin)
N.C.    Negative control (protein solution of host bifidobacterium)
Sample  Protein solution of transformed bifidobacterium
M      Molecular weight marker

GENE EXPRESSING A BIFIDOBACTERIUM SURFACE-PRESENTED FUSION PROTEIN

TECHNICAL FIELD

The present invention relates to a technique for expressing and displaying a protein or a peptide on the surface of a *bifidobacterium* and a novel vaccine produced from a *bifidobacterium* using this technique.

BACKGROUND ART

A cell membrane is a biomembrane that separates the inside and the outside of a cell. Many membrane proteins having a function of providing cellular information or a function of transporting a substance inside and outside the cell are present on the surface of the cell membrane. In recent years, it has been found that membrane proteins are playing important roles in immunity, and that membrane proteins on the cell surface are targeted in antigen-antibody reactions. A concept is therefore proposed that a specific antigen should be fused with a membrane protein and displayed on the surface of a microbial cell to be used as an oral vaccine to artificially induce an antigen-antibody reaction. At present, however, no example of such use has been reported in practice, and only a few examples of application have been described in research papers. For example, an enzyme protein, such as poly-γ-glutamic acid synthetase, is displayed on the cell surface of a host microorganism utilizing a vector including a gene coding for a membrane-binding site (Patent Document 1). However, only lactic bacteria, yeast, and *Escherichia coli* have been reported as hosts.

Microorganisms belonging to the genus *Bifidobacterium* (these bacteria are collectively referred to as "bifidobacteria") are indigenous bacteria that are present in the lower part of the small intestine or in the large intestine of humans and other animals. As bifidobacteria are obligate anaerobic Gram-positive bacteria, bifidobacteria grow in highly selective culture media (aerobic bacteria do not grow), have high affinity for organisms (predominant in the intestines of infants and also abundant in the intestines of adults), and do not have endotoxins unlike Gram-negative bacteria (highly safe). Accordingly, bifidobacteria are generally recognized as safe (GRAS). As some reports show that *Bifidobacterium longum* binds to mucus comprising mucins, which covers the intestinal tract, bifidobacteria are thought to be more adhesive to the intestinal wall than other bacteria in the intestines.

Although bifidobacteria attract much attention as described above, expression systems for displaying proteins on the cell surface of bifidobacteria have not yet been developed.

PRIOR ART DOCUMENTS

Patent Documents

Patent Document 1: Japanese National Publication No 2005-500054
Patent Document 2: Japanese Patent Publication No. 3642755 Non-Patent Documents
Non-Patent Document 1: Suzuki R. et al., J. Biol. Chem., 2008, vol. 283, p. 13165
Non-Patent Document 2: McClelland M. et al., Nature, 2001, vol. 413, p. 852
Non-Patent Document 3: Heidelberg et al., Nature, 2000, vol. 406, p. 477
Non-Patent Document 4: Tominaga A. et al., Genes Genet. Syst., 2001, vol. 76, p. 111
Non-Patent Document 5: Wada J. et al., Acta Crystallographica Section F., 2007, vol. F63, p. 751

SUMMARY OF INVENTION

Problems to be Solved by the Invention

An object of the present invention is to provide a means of expressing and displaying a protein or a peptide on the cell surface of a *bifidobacterium*.

Means for Solving the Problems

As a membrane protein generally forms a three-dimensional structure only on the cell membrane, it was difficult to analyze the three-dimensional structure as a single protein and to intentionally display fusion proteins including such membrane proteins on the surface. In recent years, however, the three-dimensional structure of GNB/LNB substrate-binding membrane protein (hereinafter referred to as GL-BP) present in the cell membrane of bifidobacteria was analyzed (Non-Patent Document 1). The inventors of the present invention paid attention to GL-BP and conducted various researches on the usage of surface display of target proteins. As a result, they successfully provided a means of expressing and displaying a protein on the cell membrane of a *bifidobacterium*.

The present invention provides a gene for expressing a target protein or peptide on a surface of a *bifidobacterium*, wherein a gene coding for a *bifidobacterium*-derived GNB/LNB substrate-binding membrane protein and a gene coding for the target protein or peptide are linked in this order from the 5' end side.

In one embodiment, the above-mentioned target protein or peptide is an antigen protein or an antigen peptide.

In a further embodiment, the above-mentioned antigen protein or peptide is a *salmonella*-derived flagellin, and in another embodiment, the above-mentioned antigen protein or peptide is an M2 protein of an influenza virus.

In one embodiment, the above-mentioned gene for expressing a target protein or peptide on a surface of a *bifidobacterium* comprises a gene coding for a protein having an adjuvant function between the above-mentioned gene coding for a GNB/LNB substrate-binding membrane protein and the above-mentioned gene coding for a target protein or peptide.

In one embodiment, the above-mentioned protein having an adjuvant function is a flagellin.

The present invention also provides a plasmid for gene expression, comprising any one of the above-mentioned gene for expressing a target protein or peptide on a surface of a *bifidobacterium* in an expressible form.

Further, the present invention provides a transformed *bifidobacterium*, harboring the above-mentioned plasmid and displaying a target protein or peptide on a cell surface.

Further, the present invention provides a transformed *bifidobacterium*, comprising in a genome any one of the above-mentioned gene for expressing a target protein or peptide on a surface of a *bifidobacterium* in an expressible form and displaying the above-mentioned target protein or peptide on a cell surface.

In one embodiment, the above-mentioned target protein or peptide is a *salmonella*-derived flagellin.

In one embodiment, the above-mentioned target protein or peptide is an M2 protein of an influenza virus.

In one embodiment, the above-mentioned transformed *bifidobacterium* further displays a protein having an adjuvant function on a surface.

In a further embodiment, the above-mentioned protein having an adjuvant function is a flagellin.

In one embodiment, the above-mentioned target protein or peptide is an antigen protein or an antigen peptide or a protein having an adjuvant function.

The present invention also provides an oral vaccine against *salmonella* infection, comprising a transformed *bifidobacterium* displaying a *salmonella*-derived flagellin on a surface thereof.

The present invention also provides an oral influenza vaccine, comprising a transformed *bifidobacterium* displaying an M2 protein of an influenza virus on a surface thereof.

Effects of Invention

According to the present invention, a target protein or peptide can be expressed and displayed on the cell surface of a *bifidobacterium*. For example, by displaying an antigen protein or an antigen peptide of a microorganism, a virus, a protozoon, a cancer, or the like on the surface of a *bifidobacterium*, the *bifidobacterium* can be used as an oral or nasal vaccine that transports the antigen protein to the mucous membrane of the small intestine or the nose as a carrier and induces an antibody reaction with the antigen displayed on the mucous membrane.

BRIEF DESCRIPTION OF DRAWINGS

FIG. 2(*b*) is a fluorescence micrograph showing an untreated *bifidobacterium* (no GL-BP-FliC surface display).

Figure 1:
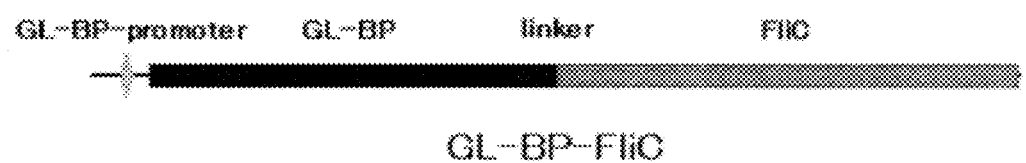
FIG. 1 is a schematic view showing a fused gene in which the flagellin (FliC) gene is ligated downstream of the GL-BP gene.

MODE FOR CARRYING OUT THE INVENTION (Bifidobacteria)

In the present invention, "bifidobacteria" refer to microorganisms belonging to the genus *Bifidobacterium*. Examples of the bifidobacteria include *Bifidobacterium adolescentis, B. angulatum, B. animalis* subsp. *animalis, B. animalis* subsp. *lactis, B. asteroides, B. bifidum, B. boum, B. breve, B. catenulatum, B. choerinum, B. coryneforme, B. cuniculi, B. denticolens, B. dentium, B. gallicum, B. gallinarum, B. globosum; B. indicum, B. infantis, B. inopinatum, B. lactis, B. longum, B. magnum, B. merycicum, B. minimum, B. parvulorum, B. pseudocatenulatum, B. pseudolongum* subsp. *globosum, B. pseudolongum* subsp. *pseudolongum, B. pullorum, B. ruminale, B. ruminantium, B. saeculare, B. scardovii, B. subtile, B. suis, B. thermacidophilum*, and *B. thermophilum*.

Of these, *Bifidobacterium adolescentis, B. animalis* subsp. *animalis, B. animalis* subsp. *lactis, B. bifidum, B. breve, B. lactis, B. longum*, and *B. pseudolongum* subsp. *pseudolongum* are preferably used.

Furthermore, resistant strains or mutant strains of these bifidobacteria may be used. Both of these bacterial strains are commercially available or readily available from depositories. Examples of the bacterial strains include *B. longum* JCM1217 (ATCC15707) and *B. bifidum* ATCC11863.

(GNB/LNB Substrate-Binding Membrane Protein)

The GNB/LNB substrate-binding membrane protein (GL-BP) is a membrane protein belonging to the ATP-binding cassette (ABC) protein family, which transports lacto-N-biose (i.e., N-acetyl-3-O-(β-D-galactopyranosyl)-D-glucosamine) and galacto-N-biose (i.e., N-acetyl-3-O-(β-D-galactopyranosyl)-D-galactosamine) of a *bifidobacterium*. ABC proteins are important membrane proteins that actively transport specific substances on the cell membranes of all organisms using an energy called adenosine triphosphate (ATP), and various ABC proteins are present on the cell membranes. Therefore, if an appropriate promoter is used, GL-BP, which is an ABC protein, is ubiquitously expressed in bacteria belonging to the genus *Bifidobacterium* (bifidobacteria), which have a cellular function for expressing GL-BP on the surface thereof. For example, GL-BP derived from the *Bifidobacterium longum* JCM1217 (ATCC15707) strain has an amino acid sequence of SEQ ID NO: 2 in the sequence listing.

The structure of GL-BP is not limited to the structure of naturally occurring GL-BP, and amino acids constituting the GL-BP may include one or more of substitutions, insertions or deletions, so long as the GL-BP has an ability of being expressed on the cell surface of a *bifidobacterium*.

(Target Protein or Peptide)

The target protein or peptide to be displayed on the surface of a *bifidobacterium* is not particularly limited. The target protein or peptide is preferably a protein or a peptide that is by nature not localized on the cell surface but is arranged on the cell surface for cell surface display. Examples of the target protein or peptide include antigen proteins or peptides and enzymes. The structure of the target protein or peptide is not limited to the structure of a naturally occurring protein or peptide, and amino acids constituting the protein or the peptide may include one or more of substitutions, deletions, or additions, so long as the protein or the peptide achieves a target function.

Examples of the antigen protein or peptide include antigen proteins or antigen peptides derived from bacteria, viruses, protozoa, and the like. Examples of bacteria include bacteria that can cause bacterial infection, such as *salmonella* bacteria, *Salmonella typhimurium*, dysentery bacteria, *Diplococcus pneumoniae*, and tuberculosis bacteria. Examples of viruses include various types of influenza viruses, herpes viruses, SARS virus, AIDS virus, and various hepatitis viruses. Examples of protozoa include malaria, trichomonad, and toxoplasma. More specific examples of the antigen protein or peptide include flagellin proteins of *salmonella* bacteria and of *Salmonella typhimurium*, the M2 protein of influenza virus, the serine repeat antigen (SERA) protein of malaria protozoa, the GBS80 protein of group B *streptococcus*, which causes group B *streptococcus* infection in neonates, the pg40 envelope protein of *Porphyromonas gingivalis*, which is a causative bacterium of periodontal disease, the gp120 or gp160 envelope proteins of HIV, the E6, E7 or L2 proteins of human papillomavirus, which cause endocervical cancer, the E2/NS1 envelope glycoprotein of hepatitis C virus (HCV), the NS1 nonstructural protein or the DI, DII and DIII protein of viruses belonging to the genus *Flavivirus*, which cause Japanese encephalitis, amyloid beta (Aβ) protein, which causes Alzheimer's disease, the gp53 protein of viruses belonging to the genus *Pestivirus*, which causes bovine viral diarrhea virus (BVDV), the gp55 envelope protein of hog cholera virus, the VP2 capsid protein of canine parvovirus and parvovirus which causes feline panleukopenia, and the VP28 envelope protein of white spot syndrome virus, which causes death of infected shrimp.

Examples of enzymes include glucoamylase, α-amylase, β-amylase, isoamylase, endoglucanase, exocellobiohydrolase, β-glucosidase, carboxymethylcellulase, glutamate dehydrogenase, glutamine synthetase, lipase, lysine decarboxylase, arabinofuranosidase, peroxidase, and alkaline phosphatase.

Examples of other target proteins or peptides include fluorescent proteins (GFP, SIRIUS, BFP, CFP, YFP, RFP, Venus, DsRed, mCherry, mKO, mCerulean, etc.), bioluminescence proteins (firefly luciferase, aequorin (*Aequorea victoria*), renilla luciferase, sea-firefly luciferase, etc.), aryl hydrocarbon receptors used for detecting toxic substances, His tag, protein A, and antibodies against proteins specifically expressed in patients with cancer or specific diseases (for example, Alzheimer's disease).

(Proteins having Adjuvant Function)

As proteins having an adjuvant function, flagellin proteins, which constitute a flagellum of a microorganism, are known to induce high levels of antibodies.

A flagellum is a long structure protruded from the cell surface and plays an important role in motility and invasion into a host cell. The flagellum is composed of a protein called flagellin (hereinafter may be referred to as FliC). For example, the antigenic flagellin protein of *Salmonella typhimurium* (*Salmonella enterica* subsp. *enterica* serovar *Typhimurium*) is described in Non-Patent Document 2. The antigenic flagellin protein of a cholera bacterium (*Vibrio cholerae*) is described in Non-Patent Document 3. The antigenic flagellin protein of a dysentery bacterium (*Shigella dysenteriae*) is described in Non-Patent Document 4. For example, flagellin derived from *Salmonella typhimurium* has an amino acid sequence of SEQ ID NO: 4 shown in the sequence listing. The flagellin protein may have one or more of substitutions, deletions, or additions in the constituent amino acids so long as the protein has an adjuvant function.

(Fusion Protein Displayed on Surface of *bifidobacterium*)

In the present invention, a protein or a peptide expressed and displayed on the surface of a *bifidobacterium* is expressed as a fusion protein with GL-BP. In this fusion protein, from the N terminus GL-BP and the target protein or peptide are linked in this order. If necessary, a protein having an adjuvant function may be included between GL-BP and the target protein or peptide.

(Preparation of Transformed *bifidobacterium*)

Hereafter, preparation of a transformed *bifidobacterium* in which a target protein or peptide is expressed and displayed on the *bifidobacterium* surface as a fusion protein is described in the order of the procedure.

1. Obtaining Genes Coding for Respective Proteins

The gene coding for GL-BP, the gene coding for a target protein or peptide, and the gene coding for FliC can be obtained based on the known gene sequence or amino acid sequence information. For example, these genes can be obtained by amplification through polymerase chain reaction (PCR) using genomic DNA or cDNA prepared from any *bifidobacterium* as a template and a primer pair prepared based on the sequence information of the structural gene of GL-BP of the *bifidobacterium*. In general, as one amino acid allows more than one genetic code, the gene may have a base sequence that differs from a known base sequence or a base sequences based on a known amino acid sequence.

For example, the gene coding for GL-BP of *Bifidobacterium longum* can be obtained from the structural gene sequence of GL-BP of *B. longum* described in Non-Patent Document 5. For example, the gene can be obtained by amplification through PCR using chromosome DNA or cDNA of *B. longum* as a template and a primer pair prepared based on the sequence information.

The gene coding for a target protein or peptide can be obtained based on known gene sequence information or amino acid sequence information. For example, the gene coding for glucoamylase derived from *Rhizopus oryzae* can be obtained by amplification through PCR using genomic DNA or cDNA prepared from *R. oryzae* as a template and a primer pair prepared based on the sequence information of the structural gene of glucoamylase of *R. oryzae*.

The gene coding for FliC can be obtained based on known gene sequence information or amino acid sequence information. The gene coding for FliC can be obtained by amplification through PCR using genomic DNA or cDNA prepared from, for example, an infection pathogenic bacterium (for example, *salmonella*, cholera, or dysentery bacterium) as a template and a primer pair prepared based on the sequence information of the structural gene of FliC of the bacterium.

More specifically, the above-mentioned gene coding for each protein can be obtained by, for example, a known chemical synthesis method based on known base sequence information. Examples of the chemical synthesis method include chemical synthesis with a DNA synthesizer using phosphoramidite. Furthermore, the above-mentioned gene can also be obtained by amplification of DNA through PCR by preparing primers based on base sequences in the 5' end and the 3' end of a base sequence to be obtained and using cDNA synthesized from mRNA contained in various tissues or cells of the source organism or cDNA selected from a cDNA library as a template. Furthermore, the above-mentioned gene can be obtained by colony hybridization or plaque hybridization of cDNA synthesized from mRNA contained in various tissues or cells of the source organism or the cDNA library, using a full-length or partial DNA or polynucleotide chemically synthesized based on known base sequence information as a probe.

Furthermore, the above-mentioned gene coding for each protein can also be readily obtained based on known amino acid sequence information. Examples of methods for obtaining the above-mentioned gene coding for each protein based on known amino acid sequence information include amplification of a target gene from the above-mentioned cDNA library or the like through PCR using synthesized DNA primers having a partial base sequence of the gene coding for a known amino acid sequence, or selection by hybridization of a gene incorporated into a suitable vector with a labeled DNA fragment or synthesized DNA (probe) coding for a part or a full-length of the above-mentioned gene coding for each protein.

The above-mentioned gene coding for each protein may be a DNA that is hybridizable with a gene obtained as described above under stringent conditions. The DNA that is hybridizable under stringent conditions means a DNA obtainable by colony hybridization, plaque hybridization, southern blot hybridization, or the like using the above-mentioned DNA as a probe. Specific examples of such DNAs include a DNA that can be identified by performing hybridization at approximately 65° C. in the presence of approximately 0.7 to 1.0 M sodium chloride using a filter on which a DNA derived from a colony or a plaque is immobilized and then washing the filter using an SSC solution having an approximately 0.1 to 2-fold concentration (an SSC solution having a 1-fold concentration is composed of 150 mM sodium chloride and 15 mM sodium citrate) at approximately 65° C. Specific examples of the above-mentioned hybridizable DNA include a DNA having a homology of approximately 80% or greater, preferably a DNA having a homology of approximately 90% or greater, more preferably a DNA having a homology of approximately 95% or greater with the base sequence of the gene coding for each protein obtained based on the above-mentioned known base sequence information or amino acid sequence information.

2. Preparation of Vector for Transformation of *bifidobacterium*

A recombinant DNA including the gene coding for each protein, prepared as described in the above 1, is prepared. In the present invention, a recombinant DNA can be an expression vector or a chromosome-incorporation vector (for example, a homologous recombinant vector). A plasmid used for preparing such vectors is not particularly limited so long as the plasmid can be expressed in a *bifidobacterium*. Examples of plasmids derived from bifidobacteria that can be used include pTB6, pBL67, pBL78, pNAL8H, pNAL8M, pNAC1, pBC1, pMB1, and pGBL8b. Composite plasmids of these plasmids and plasmids derived from *Escherichia coli* can also be used, and examples thereof include pBLES100, pKKT427, and pRM2.

Among the above-mentioned plasmids, composite plasmids synthesized from plasmids of *B. longum* and plasmids of *E. coli* are preferred from the viewpoint of stabile expression and easy DNA preparation for preparation of a transformant strain.

Expression vectors preferably have a selectable marker such as antibiotic resistance or amino acid auxotrophy from the viewpoint of selection of a transformant strain.

Expression vectors preferably include a regulatory sequence for the expression of the fusion protein of GL-BP and a target protein or peptide, or for the vectors to be advantageous to expression. Examples of regulatory sequences include promoter sequences, leader sequences, propeptide sequences, enhancer sequences, signal sequences, and terminator sequences. The origin of these regulatory sequences is not particularly limited so long as the vectors are expressed in a *bifidobacterium*.

The promoter sequences are not particularly limited so long as the vectors are expressed in a *bifidobacterium*. From the viewpoint of expression efficiency, the promoter sequence of a histone-like protein (HU), LDH promoter, and the like of *B. longum* are preferably used.

Expression vectors preferably have a terminator sequence from the viewpoint of improving expression efficiency. The terminator sequence of the above-mentioned HU gene is preferably used as a terminator sequence.

In addition, a leader sequence, a propeptide sequence, an enhancer sequence, a signal sequence, and the like can be arranged as required. Furthermore, a gene coding for a linker having an appropriate length may be positioned between the gene coding for GL-BP and the gene coding for a target protein or peptide.

Thus, a cloning vector is prepared by introducing regulatory sequences such as a promoter sequence and a terminator sequence and a selectable marker gene into the above-mentioned plasmid as required. Examples of the selectable marker include antibiotic resistance markers such as spectinomycin (SPr), ampicillin (Ampr), tetracycline (TETr), kanamycin (KMr), streptomycin (STr), and neomycin (NEOr); fluorescent markers such as green fluorescent protein (GFP) and red fluorescent protein (REP); and enzymes such as LacZ.

A cloning vector preferably has, for example, a linker having a multicloning site downstream of the promoter. By using such a linker, the gene (DNA) coding for the above-mentioned fusion protein is incorporated downstream of the promoter so that the fusion protein can be expressed in-frame. Representative examples of a plasmid for a cloning vector include pBLES100 and pBLEM100 (refer to Patent Document 2).

A vector that expresses a fusion protein on the surface of a *bifidobacterium* can be obtained by incorporating in-frame the HU promoter sequence, the gene coding for GL-BP, and the gene coding for a target protein or peptide obtained as described above into the plasmid pBLES100. An expression vector as obtained by such a method is used for transformation of a *bifidobacterium*.

3. Preparation of Transformed *bifidobacterium* Expressing Fusion Protein

A recombinant DNA, for example, an expression vector is introduced into a host *bifidobacterium*. Any known transformation method can be used. Specific examples include electroporation, calcium phosphate method, lipofection, calcium ion method, protoplast, microinjection, and particle gun. In the present invention, electroporation is preferably used. Electroporation can be performed at 0.5 to 20 kV/cm for 0.5 µsec to 10 msec, more preferably at 2 to 10 kV/cm for 50 µsec to 5 msec.

A transformed strain is selected with a selectable marker contained in the fusion protein expression vector. A medium for culturing the transformed strain may be any medium suitable for the host microorganism. Examples of the medium include blood liver (BL) agar medium, de Man-Rogosa-Sharpe (MRS) agar medium, Gifu anaerobic medium (GAM) agar medium, improved GAM (TGAM) agar medium, Briggs agar medium, and yeast glucose peptone (YGP) agar medium. For selection pressure, antibiotics can be added to the medium, or amino acids can be deleted from or added to the medium, depending on the selectable marker.

Culture is preferably performed under an anaerobic condition under which bifidobacteria can be cultured. Growth of aerobic bacteria can be prevented by performing culture under an anaerobic condition. An example of anaerobic conditions is the condition in a sealed container in which anaerobicity sufficient to grow bifidobacteria can be maintained, for example, conditions that can be achieved in an anaerobic chamber or an anaerobic box. It is sufficient that the culture temperature is a temperature at which bifidobacteria can be cultured. The culture temperature is usually 4° C. to 45° C., preferably 15° C. to 40° C., more preferably 24° C. to 37° C.

A transformed *bifidobacterium* may be prepared in which not only a vector for surface display of a fusion protein of GL-BP and a target protein or peptide, but also a vector for surface display of a fusion protein of GL-BP and a protein having an adjuvant function are simultaneously introduced.

Introduction of a gene coding for a fusion protein may be confirmed by extracting a plasmid from a transformed *bifidobacterium*, treating the plasmid with restriction enzymes, and then performing electrophoresis or directly sequencing the sequence of the restriction enzyme-treated fragment.

The expression of the fusion protein of a transformed *bifidobacterium* obtained can be confirmed, for example, using the Western blotting. First, the transformed *bifidobacterium* is lysed, for example, using a non-ionic surfactant, including polyoxyethylene sorbitan ester (Tween (registered trademark) 20, 40, 60, 65, 80, 85), and sorbitan ester (Span (registered trademark) 20, 40, 60, 65, 80, 85), and the like; then diluted with phosphate buffer, citrate buffer, borate buffer, tris(hydroxymethyl)aminomethane (Tris)-hydrochloride buffer, or the like; then subjected to electrophoresis with sodium dodecyl sulfate-polyacrylamide gel (SDS-PAGE), tris-glycine-polyacrylamide gel, or the like; then transferred to nitrocellulose membrane, polyvinylidene fluoride (PVF) membrane, or the like; and then reacted with an antibody (immunoglobulin G (IgG)) against the target protein or peptide, and further reacted with a secondary antibody with a fluorescent label. Thereby, expression of the fusion protein can be confirmed.

In particular, the display of a target protein or peptide on the *bifidobacterium* surface can be easily confirmed by performing on the transformed *bifidobacterium* an immunoantibody method using an antibody against the target protein or peptide and an FITC-labeled anti-IgG antibody. When a fusion protein of GL-BP, a protein having an adjuvant function, and a target protein or peptide is expressed, since the protein having an adjuvant function and the target protein or peptide are displayed on the surface of *bifidobacterium*, the antibody used for confirmation may be an antibody against either protein (or peptide).

The transformed *bifidobacterium* in which surface display of the target protein or peptide has been confirmed may be cultured, recovered, and used directly for the production of a formulation, using any methods commonly used by those skilled in the art. Alternatively, the transformed *bifidobacterium* may be used in a dry form. The transformed *bifidobacterium* can be dried by the treatment in which a low-temperature treatment such as freeze drying or low-temperature drying is performed so that the *bifidobacterium* can grow when exposed to growth conditions such as those in an intestinal environment or a medium.

The transformed *bifidobacterium* may be subjected to post-treatment performed according to a known method. For example, rough purification may be performed by centrifugation or the like. Furthermore, after rough purification, the transformed *bifidobacterium* may be dissolved or suspended in a solvent conventionally used in this field, such as physiological saline, phosphate-buffered saline (PBS), or lactated Ringer's solution, if desired. Furthermore, lyophilization or spray drying may be performed to powder and granulate the transformed *bifidobacterium*, if desired.

(Formulation Containing Transformed *bifidobacterium*)

When the target protein or peptide displayed on the surface is administered preferably for the treatment or prevention of a disease, the transformed *bifidobacterium* of the present invention is administered in any formulation form. The administration route is not particularly limited, and examples of the administration route include oral administration and parenteral administration. When the target protein or peptide is an antigen protein or peptide, oral or nasal administration is preferred.

Examples of a formulation suitable for oral administration include tablet, granule, fine granule, powder, syrup, solution, capsule, and suspension. Examples of a formulation suitable for parenteral administration include injection, drip infusion, inhalant, spray, suppository, percutaneous absorbing agent, and transmucosal absorbing agent.

For production of a liquid formulation for oral administration, for example, formulation additives including saccharides such as water, sucrose, sorbit, and fructose; glycols such as polyethylene glycol and propylene glycol; oils such as sesame oil, olive oil, and soybean oil; and preservatives such as p-hydroxybenzoic acid esters can be used. Furthermore, for example, excipients such as lactose, glucose, sucrose, and mannitol; disintegrating agents such as starch and sodium alginate; lubricants such as magnesium stearate and talc; binders such as polyvinyl alcohol, hydroxypropylcellulose, and gelatin; surfactants such as fatty acid esters; and plasticizers such as glycerine can be used for production of a solid formulation such as capsule, tablet, powder, or granule.

Among formulations for parenteral administration, formulations for intravascular administration such as injection and drip infusion can be preferably prepared using an aqueous vehicle that is isotonic with human blood. For example, injections can be prepared as a solution, suspension, or dispersion using an aqueous vehicle selected from a salt solution, a glucose solution, or a mixture of a salt solution and a glucose solution, together with an appropriate auxiliary agent according to a usual method. Suppositories for enthral administration can be prepared using a carrier such as cacao butter, hydrogenated oil and fat, or hydrogenated fatty acid.

Among formulations for parenteral administration, sprays can be prepared using a carrier that does not stimulate mucous membranes of the human oral cavity and respiratory tract and can promote absorption by dispersing a transformed *bifidobacterium*, an active ingredient, as fine particles. Examples of such a carrier include lactose and glycerine. Depending on the properties of a transformed *bifidobacterium* and a carrier to be used, a formulation can be prepared in the form of an aerosol, dry powder, or the like. One or more formulation additives selected from, for example, diluents, flavors, preservatives, excipients, disintegrating agents, lubricants, binders, surfactants, plasticizers, and the like can be used for production of a formulation for parenteral administration.

(Oral Vaccine)

When the target protein or peptide is an antigen protein in the present invention, a transformed *bifidobacterium* is preferable as an oral vaccine. For example, when the antigen protein is a flagellin, the flagellin is recognized at the intestinal tract wall as an antigen, and thus an antibody is produced. Therefore, an oral vaccine effective for infection with a microorganism having flagellins is produced.

For example, when an acid-resistant capsule formulation (seamless capsule formulation, soft capsule formulation, or hard capsule formulation) described below is orally administered, the formulation passes through the stomach, which has pH 1 to 3, without being dissolved and reaches the intestines where the capsule formulation is dissolved. After the capsule is dissolved, a transformed *bifidobacterium* released from the formulation grows in the enteric environment and displays the target protein or peptide on the surface thereof.

(Production of Acid-Resistant Capsule Formulation Containing Transformed *bifidobacterium*)

The oral vaccine of the present invention is preferably in the form of a capsule formulation. In the present specification, a capsule containing the content is referred to as a "capsule formulation." The capsule formulation in the present invention is composed of a capsule membrane and a transformed *bifidobacterium* that expresses a target protein or peptide on the surface thereof. This capsule membrane is resistant to acids. A capsule formulation composed of an acid-resistant capsule membrane and a transformed *bifidobacterium* that expresses a target protein or peptide on the surface thereof may have any configuration and shape, and it is not precluded that the capsule formulation contains further components, so long as the capsule formulation has an acid-resistant capsule membrane and a transformed *bifidobacte-*

*rium* that expresses a target protein or peptide on the surface thereof as a capsule content. Therefore, the transformed *bifidobacterium* that expresses a target protein or peptide on the surface thereof is encapsulated with or enveloped in an acid-resistant capsule membrane (i.e., contained in the internal region of a capsule formed by the acid-resistant membrane). In the present specification, this capsule formulation is also referred to as an "acid-resistant capsule formulation."

In order that the transformed *bifidobacterium* expresses a target protein or peptide on the surface thereof to function as an oral vaccine, the transformed *bifidobacterium* must pass through the stomach, reach the intestines, and grow in the intestines. Meanwhile, pH of the stomach is 1 to 3. Most of orally ingested bifidobacteria die due to this markedly low pH. It is generally said that less than one ten thousandth of a *bifidobacterium* dose reaches the intestines while maintaining the growth ability. Therefore, in order that the transformed *bifidobacterium* used in the present invention survive and reach the human intestines and grow in the intestines to express a target protein or peptide, it is preferable that the transformed *bifidobacterium* is unlikely to be affected by gastric acid.

To this end, the transformed *bifidobacterium* is preferably included or encapsulated by an acid resistant capsule membrane in the present invention. Specifically, a capsule formulation in which the transformed *bifidobacterium* is contained inside the capsule with an acid resistant membrane is provided. The configuration, shape, and the like of the capsule formulation are not particularly limited so long as the membrane is resistant to gastric acid. That is, it is desirable to configure the capsule formulation so that gastric acid does not enter the capsule or is not brought into contact with the transformed *bifidobacterium*. The capsule membrane can be a membrane that is not dissolved at pH 4 or lower, preferably pH 1 to 3. Methods for encapsulation are also not particularly limited.

(Seamless Capsule Formulation)

The capsule for providing with resistance to gastric acid may be preferably in the form of a seamless capsule. Herein, "seamless capsule" refers to a type of soft capsule in which the contents are enveloped in a seamless membrane. The seamless capsule can have a multi-layered structure consisting of two or more layers, and preferably has a multi-layered structure consisting of three or more layers. Topically, an innermost layer can contain the contents (being the transformed *bifidobacterium* in the case of the present invention), and an outer layer (or the outermost layer) can act as the membrane. Specifically, the transformed *bifidobacterium* is encapsulated with the membrane.

Figure 7:
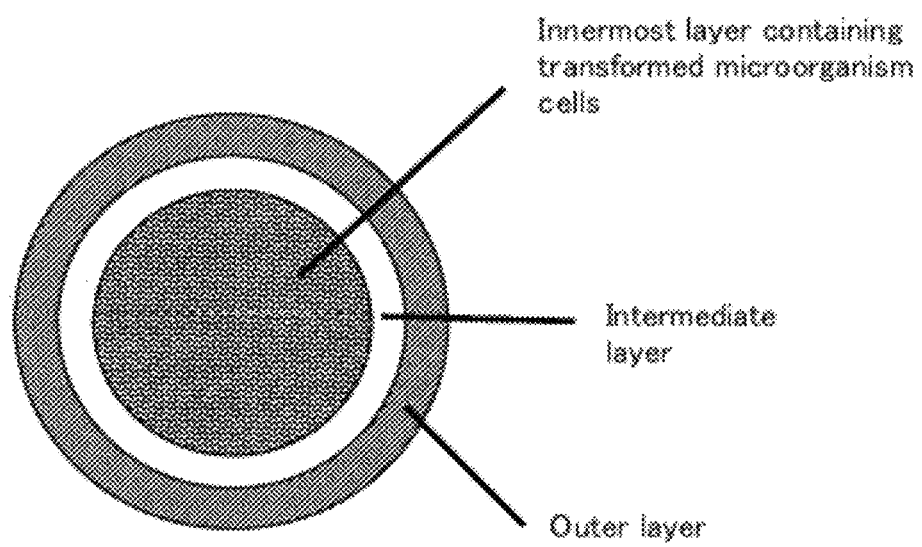
FIG. 7 is a schematic cross view of a three-layer seamless capsule formulation.

Hereinafter, preparation of a three-layered seamless capsule formulation will be described. FIG. 7 is a schematic cross-sectional view of a three-layered seamless capsule formulation. This three-layered structure consists of an innermost layer, an intermediate layer that covers the innermost layer, and an outer layer that covers the intermediate layer.

The innermost layer consists of the transformed *bifidobacterium* and a non-aqueous solvent or solid component for suspending or mixing the transformed *bifidobacterium* (hereinafter, which component is referred to as an "innermost layer substance"). There is no particular limitation on the innermost layer substance. Examples thereof include various fat and oils, fatty acids, fatty acid esters of sugars, aliphatic hydrocarbons, aromatic hydrocarbons, linear ethers, higher fatty acid esters, higher alcohols, and terpenes. Specific examples thereof include, but are not limited to, soybean oil, sesame oil, palm oil, palm kernel oil, corn oil, cottonseed oil, coconut oil, rapeseed oil, cacao butter, beef tallow, lard, horse oil, whale oil, hydrogenated fat and oils of these natural fat and oils having a melting point of 40° C. or lower, margarine, shortening, glycerin fatty acid esters, sucrose fatty acid esters, camphor oil, peppermint oil, α-pinene, D-limonene, and the like. These innermost layer substances can be used alone or in a combination of two or more.

A material used for the intermediate layer is, among the above-listed innermost layer substances, a material having a melting point of 20° C. to 50° C. and different from the innermost layer substance, more preferably a material which is in solid state at ambient temperatures. As, in the examples set forth below, hydrogenated palm kernel oil having a melting point of 34° C. and hydrogenated palm kernel oil having a melting point of 43° C. are used as the innermost layer substance and the inner layer material, respectively, the same species of fat and oils may be used as the innermost layer substance and the inner layer material, which are subjected to hydrogenation so as to have different melting points. This intermediate layer can act as preventing the permeation of water and oxygen and preventing contact with gastric acid. The material to be selected may be determined in consideration of the storage period of the capsule and the like.

A material used for the outer layer (being the outermost layer in the case of a structure having three or more layers) may be a mixture of a protein and a water-soluble polyhydric alcohol; a mixture of a protein, a water-soluble polyhydric alcohol, and a polysaccharide; a mixture of a polysaccharide and a water-soluble polyhydric alcohol; or the like. Examples of the protein include gelatin and collagen. Examples of the water-soluble polyhydric alcohol include sorbitol, mannitol, glycerin, propylene glycol, and polyethylene glycol. Examples of the polysaccharide include agar, gellan gum, xanthan gum, locust bean gum, pectin, alginate, carrageenan, gum arabic, dextrin, modified dextrin, starch, modified starch, pullulan, pectin, and carboxymethylcellulose salt. In the case where pectin, alginate, gellan gum, or carrageenan is used, an alkali metal salt or an alkaline-earth metal salt may be added as appropriate.

The three-layered seamless capsule formulation is prepared using any techniques known by those skilled in the art, such as the dropping method using a triple nozzle described in Japanese Patent No. 1398836. In this dropping method, the innermost layer substance combined with the transformed *bifidobacterium* (e.g., the freeze-dried cells of the *bifidobacterium*), which is preferably a suspension of the transformed *bifidobacterium* (preferably, the freeze-dried cells of the *bifidobacterium*) in a hydrophobic solvent material that is non-fluid at 20 to 50° C., from the innermost nozzle of the concentric triple nozzle, a material forming the intermediate layer (e.g., a liquid obtained by melting a material in the form of a solid at room temperature) from the intermediate nozzle, and a solution of a material forming the outer layer (membrane) from the outermost nozzle are simultaneously ejected, and dropped into a carrier liquid (e.g., corn oil, rapeseed oil, or the like) which flows under cooling down, thereby forming a three-layered "seamless" capsule in which the transformed *bifidobacterium* is contained in the innermost layer. Accordingly, the transformed *bifidobacterium* is encapsulated with or enveloped in the seamless outer membrane.

The capsule formed as described above is then dried. For example, the drying is performed by ventilation at ambient temperatures. Typically, the capsule is dried, for example, in the air at 5° C. to 30° C. The drying time is preferably 2 to 12 hours. As described in Japanese Laid-Open Patent Publication No. 07-069867, a capsule that has been ordinarily dried as described above may be preferably further subjected to vacuum drying or vacuum freeze drying. The degree of vacuum can be kept at 0.5 to 0.02 torr. The capsule can be frozen and dried at −20° C. or lower in the case of vacuum freeze drying. There is no particular limitation on the time for vacuum drying or vacuum freeze drying, but the time is typically 5 to 60 hours, preferably 24 to 48 hours. If the time is 5 hours or shorter, drying is insufficient and water present in the capsule may negatively affect the contents.

In the case of a capsule obtained using the method as described in Japanese Laid-Open Patent Publication No. 07-069867, water is sufficiently removed from the capsule by vacuum freeze drying, and, thus, the Aw value can be 0.20 or less, and the heat conductivity can be 0.16 kcal/mh° C. or less. By vacuum drying or vacuum freeze drying, the amount of water is naturally reduced while the capsule is sufficiently dried and becomes porous. Thus, the heat conductivity is significantly lower than that in the case where ordinary drying is simply performed.

The Aw value refers not to an absolute content of water present in the sample, but to a value determined by the state in which water is present, that is, the degrees of freedom for water in the sample. The Aw value is an indicator indicating water that can directly affect chemical reaction or microorganism growth, and is measured using an electrical-resistance-type water activity measuring method (e.g., Aw meter WA-360, Shibaura Electronics Co., Ltd.). The heat conductivity is measured using the Fitch method or the like. The Aw value is preferably 0.20 or less, and the heat conductivity is preferably 0.02 to 0.08 kcal/mh° C.

In order to provide the capsule membrane of the seamless capsule formulation with acid resistance, an acid resistant outer layer is formed, or the membrane (the outermost layer) of the prepared seamless capsule is treated so as to be acid resistant.

Examples of the method for forming an acid-resistant outer layer include addition of pectin, alginate, gum arabic, or the like in an amount of 0.01 to 20 wt %, preferably 0.1 to 10 wt % to gelatin, agar, carrageenan, or the like, which has a gelling ability.

Examples of the method for providing the membrane (the outermost layer) of the prepared seamless capsule with acid resistant include crosslinking of the outer layer (the outermost layer) of the seamless capsule and coating of the surface of the seamless capsule, which may be performed alone or in combination.

For crosslinking of the outer layer which contains a protein, the seamless capsule is first prepared, and then sufficiently washed with water, and then, the water-washed seamless capsule is added to an aqueous solution containing a crosslinking agent. Thus, the surface of the outer layer is subjected to a crosslinking treatment. As the crosslinking agent, conventionally known crosslinking agents may be used. Examples of the crosslinking agent include formaldehyde, acetaldehyde, propionaldehyde, glyoxal, glutaraldehyde, cinnamaldehyde, vanillyl aldehyde, acetone, ethyl methyl ketone, ethylene oxide, propylene oxide, potassium alum, and ammonium alum. Typically, the outer layer is treated by adding 1 part by weight of seamless capsule to 50 to 100 parts by weight of aqueous solution containing 0.1 to 2 w/v %, preferably 0.5 to 2 w/v %, of a crosslinking agent, and agitating the mixture for 10 to 300 seconds. Here, the amount of crosslinking agent used and the period of time for action vary depending on the type of the crosslinking agent. After the surface of the outer membrane is subjected to the crosslinking treatment, the outer membrane is washed sufficiently with water to remove the aqueous solution containing the crosslinking agent, and water in the outer layer is dried out.

For the crosslinking of the protein-containing outer layer, the crosslinking may be performed through enzymatic treatment with transglutaminase. In this case, the outer layer is treated by adding 1 part by weight of produced seamless capsule to 50 to 100 parts by weight of aqueous solution containing 0.1 to 10 w/v %, preferably 0.5 to 2 w/v %, of enzyme, and agitating the mixture for 1 to 300 minutes. The resultant is washed with water and dried as described above.

For the coating, after the produced wet seamless capsule is dried, the seamless capsule is conventionally coated with shellac, ethylcellulose, hydroxypropylmethylcellulose, hydroxypropylcellulose, polyvinylpyrrolidone, cellulose TC-5, vinylpyrrolidone-vinyl acetate copolymer, zein, ethylene wax, or the like as the base material, and castor oil, rapeseed oil, dibutylphthalate, polyethylene glycol, glycerin, stearic acid, fatty acid ester, sorbitan palmitate, polyoxyethylene stearate, acetylated monoglyceride, or the like as the plasticizer.

The capsule membrane can be further provided with entericity. Thereby, the capsule is protected from an acidic solution and the like (such as gastric acid) in the stomach, and disintegrates in the intestine so that the transformed *bifidobacterium* is released from the inside of the capsule to sufficiently effect the production of antigen in the intestine. The capsule membrane can be provided with entericity by producing an enteric capsule as commonly practiced by those skilled in the art. A mixture of gelatin and pectin can be used as the outer layer material of the seamless capsule to make the membrane enteric. The acid-resistant outer layer is further provided with entericity by preparing through addition of pectin, alginate, gum arabic, or the like in an amount of 0.01 to 20 wt %, preferably 0.1 to 10 wt % to gelatin, agar, carrageenan, or the like, which has a gelling ability.

The seamless capsule formulation may be in the shape of a sphere due to the production method. The average particle size of the seamless capsule is 0.3 to 10 mm, preferably 1.5 to 8.0 mm.

The thus obtained seamless capsule formulation can be stored for six months or more while maintaining the activity of the transformed *bifidobacterium* at room temperature. If the formulation is stored at 10° C. or lower, extended storage for one year or more is possible.

(Soft Capsule Formulation)

As in the case of the seamless capsule formulation, a soft capsule formulation can be the encapusulation of a suspension of the transformed *bifidobacterium* in a non-aqueous solvent (as capsule contents) with a membrane sheet. The material of the membrane sheet is as mentioned for the outer layer of the seamless capsule.

A soft capsule formulation can be prepared using any known procedures, for example, as described in Japanese Patent No. 2999535. For example, using a rotary die, while the contents are injected and filled, the membrane sheet is heated through the die, so as to envelop and encapusulate the contents, thereby the encapsulation is achieved. For the action of releasing the transformed *bifidobacterium* in the intestine, an oil, which is a release agent, is removed from the resultant soft capsule through washing with a polar solvent (e.g., methanol, ethanol, propanol, or isopropanol). Subsequently, the capsule can be made acid resistant by performing the crosslinking treatment and the coating treatment in combination, or performing either one of the treatments, as in the case of the seamless capsule.

The acid-resistant membrane sheet can be also prepared based on any known methods such as through addition of pectin, alginate, gum arabic, or the like in an amount of 0.01 to 20 wt %, preferably 0.1 to 10 wt % to gelatin, agar, carrageenan, or the like, which has a gelling ability. Alternatively, the membrane sheet can be made acid resistant, by performing the crosslinking treatment and the coating treatment in combination, or performing either one of the treatments. The thus obtained acid-resistant membrane sheet can be used to produce a soft capsule formulation in which the transformed *bifidobacterium* is encapsulated with the acid-resistant membrane. For example, from the obtained acid-resistant membrane sheet a capsule is shaped, the contents are introduced into the capsule, and then a seam of the capsule is melted and joined so as to envelop the contents, using known techniques.

The soft capsule formulation may be in the shape of a sphere, an ellipse, or a rectangle. The soft capsule preferably has a major axis of 3 to 16 mm and a minor axis of 2 to 10 mm, and more preferably has a major axis of 5 to 7 mm and a minor axis of 2 to 3 mm.

The thus obtained soft capsule formulation can be stored for six months or more while maintaining the activity of the transformed *bifidobacterium* at room temperature. If the formulation is stored at 10° C. or lower, extended storage for one year or more is possible.

(Hard Capsule Formulation)

A hard capsule formulation can be produced by molding a capsule membrane into a body and a cap in advance, filling the body of capsule with contents, and combining the resultant with the cap of capsule.

Examples of the material of the membrane of the hard capsule formulation include gelatin, cellulose, pullulan, carrageenan, and cellulose derivatives such as hydroxypropylmethylcellulose. The hard capsule can be molded using any methods commonly used by those skilled in the art. The molded capsule may be commercially available capsules. The contents can be encompassed with and enveloped in the membrane.

The contents may be a mixture obtained by sufficiently mixing the transformed *bifidobacterium* with an excipient (e.g., silicic anhydride, synthetic aluminum silicate, lactose, cornstarch, or crystalline cellulose), or powders containing dried powders of the transformed *bifidobacterium*.

After the contents are contained in the capsule, the membrane of the capsule may be coated. For this coating, the materials and the methods as mentioned for the outer layer of the seamless capsule can be applied to provide the membrane with acid resistance and preferably disintegrativity in the intestine (entericity). This coating also allows the capsule membrane to seal so as to encapsulate the contents.

The acid-resistant membrane sheet can be also prepared based on any known methods such as through addition of pectin, alginate, gum arabic, or the like in an amount of 0.01 to 20 wt %, preferably 0.1 to 10 wt % to gelatin, agar, carrageenan, or the like, which has a gelling ability. Alternatively, the membrane sheet can be made acid resistant, by performing the crosslinking treatment and the coating treatment in combination, or performing either one of the treatments. The thus obtained acid-resistant membrane sheet can be used to produce a hard capsule formulation in which the transformed *bifidobacterium* is encapsulated by the acid-resistant membrane. For example, from the obtained acid-resistant membrane sheet a hard capsule is shaped, the contents are introduced into the shaped hard capsule, and then a seam of the capsule is melted and joined so as to envelop the contents, using a known technique.

The thus obtained hard capsule formulation can be stored for six months or more while maintaining the activity of the transformed *bifidobacterium* at room temperature. If the formulation is stored at 10° C. or lower, extended storage for one year or more is possible.

EXAMPLES

Hereafter, the present invention will now be more specifically described with reference to Examples. However, the scope of the present invention is not limited to the following Examples.

Example 1

Preparation of *bifidobacterium* Displaying GL-BP-FliC on Surface

A. Isolation of GL-BP Gene

To amplify the GL-BP gene from the *Bifidobacterium longum* JCM1217 (ATCC15707) genome (Accession: EU193949), PCR was performed using primers glt-f: 5'-ggggtgctgatatattggtttg-3' (SEQ ID NO: 5) and glt-r: 5'-gctcgagctcggaaacagacaggccgaagtt-3' (SEQ ID NO: 6) which allowed the stop codon to be replaced with XhoI as well as KOD-Plus-(TOYOBO). The PCR products including the amplified GL-BP gene were subjected to agarose gel electrophoresis to excise a 1989-bp PCR product, and only a GL-BP amplification fragment was isolated and purified using Wizard SV Gel and PCR Clean-Up System (Promega).

B. Construction of pMW118 Plasmid Including Isolated GL-BP Gene

The isolated and purified GL-BP gene amplification fragment was introduced into the SmaI site of pMW118 including the ampicillin resistance gene (Ampr) (Nippon Gene) to construct a plasmid. DNA Ligation Kit Ver. 2 (Takara Bio Inc.) was used for ligation. The constructed plasmid was introduced into *Escherichia coli* DH5α (Takara Bio Inc.) by the heat shock method (42° C., 30 seconds), and the bacterial cells were spread on an LB agar medium containing 100 µg/mL ampicillin (Difco) and cultured overnight at 37° C. to obtain transformed *Escherichia coli* that harbors the plasmid including the GL-BP gene. The plasmid was extracted and purified from the transformed *Escherichia coli* using Quantum Prep Plasmid Miniprep Kit (Bio-Rad), and the sequence was confirmed by sequencing to show that the recombinant plasmid into which the GL-BP gene was introduced was obtained. The obtained recombinant plasmid was designated as pJT101.

C. Isolation of FliC Gene

To amplify the FliC gene from the genome of *Salmonella typhimurium* (*Salmonella enterica* subsp. *enterica* serovar *Typhimurium*) ATCC13312 (purchased from Summit Pharmaceutical International Corporation), PCR was performed using primers fliC-f: 5'-cctcgagatggcacaagtcattaatacaaacag-3' (SEQ ID NO: 7) to which the XhoI sequence was added and fliC-r: 5'-cctcgagttaacgcagtaaagagaggacg-3' (SEQ ID NO: 8). The amplified PCR products including the FliC gene were subjected to agarose gel electrophoresis to excise a 1502-bp PCR product, and only the FliC amplification fragment was isolated and purified using Wizard SV Gel and PCR Clean-Up System.

D. Construction of Plasmid Including FliC Gene Downstream of GL-BP Gene

The FliC gene amplification fragment isolated and purified in the above C was digested with a restriction enzyme XhoI. The FliC gene amplification fragment digested with XhoI was introduced into the above-mentioned pJT101 plasmid similarly digested with the restriction enzyme XhoI using DNA Ligation kit Ver. 2 to construct a plasmid. The constructed plasmid was introduced into *Escherichia coli* DH5α by the heat shock method, and the bacterial cells were spread on an LB agar medium containing 100 µg/mL ampicillin and cultured overnight at 37° C. to obtain a transformed *Escherichia coli* that harbors the plasmid including a fusion gene of the GL-BP gene and the FliC gene (FIG. 1). The plasmid was extracted and purified from the transformed *Escherichia coli* using Quantum Prep Plasmid Miniprep Kit, and the sequence was confirmed by sequencing to show that the recombinant plasmid in which the FliC gene was ligated downstream of the GL-BP gene was obtained. The obtained recombinant plasmid was designated as pJT102.

E. Construction of *Escherichia coli-bifidobacterium* Shuttle Vector

To shorten the sequence while maintaining the *bifidobacterium* replication origin on an *Escherichia coli-bifidobacterium* shuttle vector pBLES100, PCR was performed using pBLES100 (Matsumura H. et al., Biosci. Biotech. Biochem., 1997, vol. 61, pp. 1211-1212) as a template and pBLES-f: 5'-agggacttgatctgctcatccag-3' (SEQ ID NO: 9) and pBLES-r: 5'-ttcccattaaataataaaacaaaaaaat-3' (SEQ ID NO: 10) as primers. The PCR amplification products were subjected to agarose gel electrophoresis to excise the PCR product using Wizard SV Gel and PCR Clean-Up System, and only the PCR amplification fragment was isolated and purified. After purification, self-ligation was performed using DNA Ligation Kit Ver. 2.1 (Takara Bio Inc.). The plasmid obtained by self-ligation was designated as pTK1751. PCR was performed using pTK1751 as a template and pBLES-f3581: 5'-tagtttgcg-caacgttgttgcc-3' (SEQ ID NO: 11) and pBLES-r93: 5'-gatttcatacacggtgcctgac-3' (SEQ ID NO: 12) as primers to obtain a PCR product including the spectinomycin resistance gene (SPr) and the *bifidobacterium* replication origin ori region, which was purified by the ethanol precipitation method. Furthermore, separately, PCR was performed using pMW118 as a template and pMW118-f: 5'-atcacgaggc-cctttcgtcttc-3' (SEQ ID NO: 13) and pMW118-r: 5'-cctgttc-tattaggtgttacatgc-3' (SEQ ID NO: 14) as primers to obtain a PCR product including the *Escherichia coli* replication origin ori region, which was purified by the ethanol precipitation method. These two PCR products were ligated using DNA Ligation Kit Ver. 2.1. The obtained plasmid was introduced into *Escherichia coli* DH5α by the heat shock method, and the bacterial cells were spread on an LB agar medium containing 70 μg/mL spectinomycin and cultured overnight at 37° C. to obtain a transformed *Escherichia coli* that harbors the plasmid including the *Escherichia coli* replication origin ori region, the spectinomycin resistance gene (SPr), and the *bifidobacterium* replication origin ori region. The plasmid was extracted and purified from the obtained transformed *Escherichia coli* using Quantum Prep Plasmid Miniprep Kit to obtain the recombinant plasmid including the *Escherichia coli* replication origin ori region, the spectinomycin resistance gene (SPr), and the *bifidobacterium* replication origin ori region. The obtained recombinant plasmid was designated as shuttle vector pJW241.

F. Incorporation of Gene Obtained by Ligating GL-BP Gene and FliC Gene into *Escherichia coli-bifidobacterium* Shuttle Vector pJW241

PCR was performed using vector pJT102 having a gene obtained by linking the GL-BP gene and the FliC gene as a template and GL-BP-NdeH 5'-ccatatgaagtacgttgctttgtaaggg-gag-3' (SEQ ID NO: 15) and FliC-NdeI-r: 5'-ccatatgttaacg-cagtaaagagaggacg-3' (SEQ ID NO: 16) as primers. The PCR amplification product was purified by the ethanol precipitation method and then digested with a restriction enzyme NdeI. Separately, the *Escherichia coli-bifidobacterium* shuttle vector obtained in the above E was also digested with the restriction enzyme NdeI. The NdeI-digested PCR gene fragment and pJW241 were ligated using DNA Ligation Kit Ver. 2.1, and the obtained plasmid was introduced into *Escherichia coli* DH5α by the heat shock method, and the bacterial cells were spread on an LB agar medium containing 70 μg/mL spectinomycin and cultured overnight at 37° C. to obtain transformed *Escherichia coli* that harbors the plasmid including the *Escherichia coli* replication origin ori region, the spectinomycin resistance gene (SPr), the *bifidobacterium* replication origin ori region, and a fusion gene of the GL-BP gene and the FliC gene. The plasmid was extracted and purified from the transformed *Escherichia coli* using Quantum Prep Plasmid Miniprep Kit, and the presence of the sequence of the gene obtained by ligating the GL-BP gene and the FliC gene was confirmed. The obtained recombinant plasmid was designated as pJW245.

G. Preparation of Host *bifidobacterium* Solution

*Bifidobacterium longum* 105-A (Matsumura H. et al., Biosci. Biotech. Biochem., 1997, vol. 61, pp. 1211-1212: donated by Tomotari Mitsuoka, a professor emeritus at the University of Tokyo) was inoculated on 50 mL of a GAM medium (Nissui Pharmaceutical Co., Ltd.) and cultured at 37° C. using AnaeroPack Kenki (Mitsubishi Gas Chemical Company, Inc.). During the culture, absorbance was measured at a wavelength of 600 nm, and the culture was terminated when the absorbance reached 0.4 to 0.8. After the completion of culture, the culture broth was centrifuged at 6000×g for 10 minutes using a high-speed centrifuge to collect bacterial cells. The collected bacterial cells were washed 2 or 3 times by being suspended in 10 mL of 10% (v/v) glycerol solution and centrifuged using a high speed centrifuge.

H. Preparation of *bifidobacterium* Displaying GL-BP-FliC on Surface by Transforming *bifidobacterium* with Recombinant Plasmid pJW245

A solution of the host *bifidobacterium* obtained in the above G was suspended in 500 μL of 10% (v/v) glycerol solution. Two hundred μL of this suspension was poured into a separate tube, 5 μL of a solution containing the recombinant plasmid pJW245 obtained in the above F was added and mixed, and the mixture was allowed to stand on the ice for 5 minutes. Then, the mixture was placed in a 0.2-cm electroporation cuvette (Bio-Rad) and subjected to electroporation using Gene Pulser X Cell Electroporation System (Bio-Rad) under conditions of 2 kV, 2.5 μF, and 200Ω. Immediately after the electroporation, 0.8 mL of a GAM medium heated beforehand to 37° C. was added, and the cells were cultured using AnaeroPack Kenki at 37° C. for 3 hours. Then, the culture broth was spread on a GAM agar medium containing 70 μg/mL spectinomycin (Nissui Pharmaceutical Co., Ltd.), and the bacterial cells were cultured at 37° C. using AnaeroPack Kenki to obtain a transformed *bifidobacterium*. The obtained transformed *bifidobacterium* was inoculated on a GAM agar medium containing 70 μg/mL spectinomycin and cultured at 37° C. using AnaeroPack Kenki. After the completion of culture, the culture broth was divided into 1.5-mL tubes and suspended in an equal amount of 50% (v/v) glycerol solution. The obtained suspension was stored at −80° C. to prepare a frozen bacterial stock, which was used as a master cell of the *bifidobacterium* displaying GL-BP-FliC on the surface thereof (may also be referred to as transformed *bifidobacterium*).

Example 2

Confirmation of Surface Display of GL-BP-FliC on Transformed *bifidobacterium*-1

The frozen stock of the transformed *bifidobacterium* obtained in the above Example 1 was thawed, and the bacterial cells were cultured in a GAM medium containing 70 µg/mL spectinomycin. The obtained culture broth of the transformed *bifidobacterium* was centrifuged with a high-speed centrifuge to collect the bacterial cells. The collected bacterial cells were suspended in a PBS buffer (Nippon Gene Co., Ltd.) and washed 3 times by centrifugation with a high-speed centrifuge. Then, a primary antibody Anti-FliC Mouse Antibody (BioLegend, Inc.) was added to PBS containing 1% (w/v) BSA, the mixture was suspended in the bifidobacterial solution, and the suspension was allowed to stand at 37° C. for 30 minutes. The bacterial suspension allowed to stand for 30 minutes was centrifuged with a high-speed centrifuge to collect the bacterial cells. The collected bacterial cells were suspended in PBS and washed twice by centrifugation with a high-speed centrifuge. Then, a secondary antibody Alexa Fluor™ 488 Rabbit Anti-Mouse IgG Antibody (Molecular Probes) was added to PBS containing 1% (w/v) BSA, and the mixture was suspended in the bifidobacterial solution, and the suspension was allowed to stand at 37° C. for 30 minutes. The bacterial suspension allowed to stand for 30 minutes was centrifuged with a high-speed centrifuge to collect the bacterial cells. The collected bacterial cells were suspended in PBS, washed twice by centrifugation with a high-speed centrifuge, and then observed under a fluorescence microscope (KEYENCE). The results are shown in FIG. 2.

Figure 2:
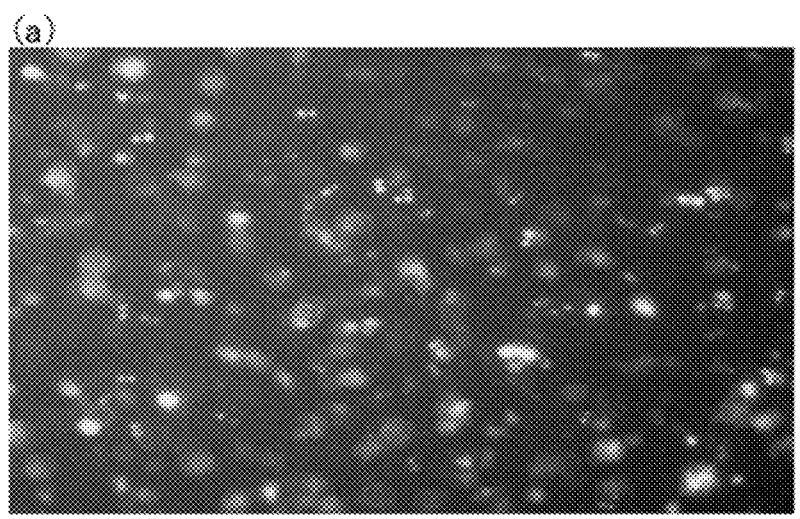
FIG. 2(*a*) is a fluorescence micrograph showing a transformed *bifidobacterium* (GL-BP-FliC surface display) obtained in Example 1.
Figure 2:
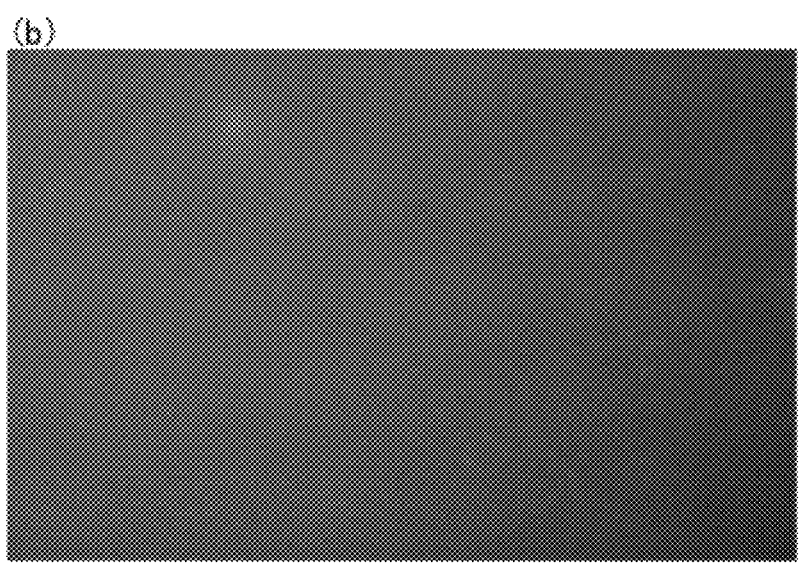

FIG. 2(*a*) is a fluorescence micrograph showing the transformed *bifidobacterium* (displaying GL-BP-FliC on the surface thereof) obtained in the above Example 1. FIG. 2(*b*) is a fluorescence micrograph of the host *bifidobacterium* (not displaying GL-BP-FliC on the surface thereof). The presence of FliC on the cell surface of the transformed *bifidobacterium* was confirmed from these fluorescence micrographs.

Example 3

Confirmation of Surface Display of GL-BP-FliC on Transformed *bifidobacterium*-2

The frozen stock of the transformed *bifidobacterium* obtained in the above Example 1 was thawed, and the bacterial cells were cultured in a GAM medium containing 70 µg/mL spectinomycin. The cultured transformed *bifidobacterium* was centrifuged with a high-speed centrifuge to collect the bacterial cells. The collected bacterial cells were suspended in PBS and washed 3 times by centrifugation with a high-speed centrifuge. A solution containing PBS, 1 M Tris-HCl (pH 8.0) (Nippon Gene Co., Ltd.), and TRITON X-100 (Wako Pure Chemical Industries, Ltd.) was added to the bacterial cells, and the solution was allowed to stand on ice for 30 minutes. An equal amount of 2×SDS gel electrophoresis buffer was added to this solution, and the mixture was allowed to stand at 95° C. for 5 minutes to obtain a sample for electrophoresis. Then, 8% (w/v) acrylamide gel was placed on an electrophoresis apparatus (ATTO Corporation), the obtained sample was applied and subjected to electrophoresis along with a molecular weight marker at a current of 20 mA for 1.5 hours. After the electrophoresis, the gel was placed on a nitrocellulose membrane (ATTO Corporation) and loaded on a blotting apparatus (Bio-Rad) at a current of 20 mA for blotting. After the blotting, the nitrocellulose membrane was immersed in a TBS buffer (Nippon Gene Co., Ltd.) containing 4% (w/v) skim milk (BD) for 1 hour for blocking. After the blocking, the nitrocellulose membrane was washed twice with TBS. The washed nitrocellulose membrane was immersed in TBS containing 0.5% (w/v) primary antibody (Anti FliC Mouse Antibody: BioLegend) for 1.5 hours and washed 3 times with TBS. Then, the nitrocellulose membrane was immersed in TBS containing 0.5% (w/v) secondary antibody (Goat Anti-Mouse IgG Conjugated with Alkaline Phosphatase: BioLegend) for 3 hours. Then, the nitrocellulose membrane was washed 3 times with TBS, allowed to develop a color using 1-Step™ NBT/BCIP Plus Suppressor Kit (PIERCE) for 30 minutes with light shielding, and rinsed with pure water, and then the surface expression of a fusion protein of FliC and GL-BP (GL-BP-FliC) was confirmed by coloration. The results of Western blotting are shown in FIG. 3.

Figure 3:
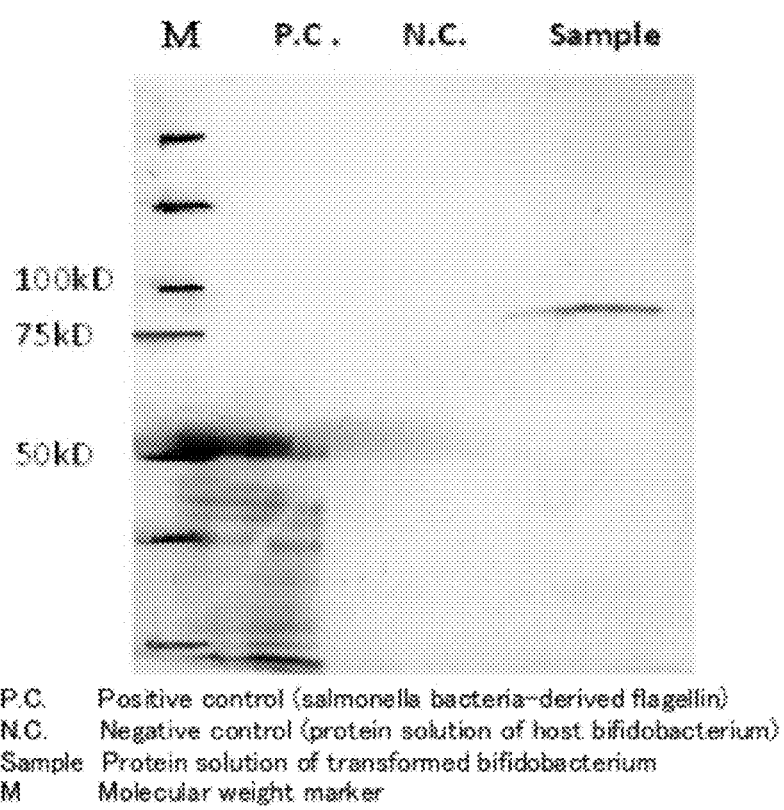
FIG. 3 is a photograph showing Western blotting of a protein solution of a transformed *bifidobacterium* (GL-BP-FliC surface display) obtained in Example 1.

As shown in FIG. 3, the sample showed a clear band at 98 kDa, which corresponds to the sum of the molecular weights of FliC and GL-BP. FliC, a positive control, showed a band at approximately 50 kD. Therefore, it was confirmed that the transformed *bifidobacterium* expressed GL-BP-FliC.

Example 4

Preparation of Transformed *bifidobacterium* for Administration to Mice

The frozen stock of the transformed *bifidobacterium* obtained in the above Example 1 was thawed, and the bacterial cells were inoculated in a GAM medium containing 70 µg/mL spectinomycin and cultured overnight at 37° C. using AnaeroPack Kenki. The culture broth was centrifuged with a high-speed centrifuge to collect the bacterial cells. The collected bacterial cells were suspended in PBS and washed twice by centrifugation with a high-speed centrifuge. Then, the bacterial cells were suspended in PBS at a concentration of $2.5 \times 10^7$ cfu/100 µL to obtain a transformed *bifidobacterium* for administration to mice.

Example 5

Confirmation of Antibody Production in Mice by Administration of Transformed *bifidobacterium*

Fifty µL of the transformed *bifidobacterium* for administration to mice prepared in the above Example 4 was orally administered to 8- to 12-week-old female BALB/c mice (Japan Charles River Laboratories Japan, Inc.) 3 times a week for 4 weeks (test group). A *bifidobacterium* into which an empty vector (pJW241 vector) was introduced as a control (control group) and 50 µL of PBS as a negative control (negative control group) were administered to mice in the same manner as for the test group. The test group, the control group, and the negative control group included 7, 6, and 5 animals, respectively.

On days 0, 14, and 28 after the start of administration, blood was collected from the caudal vein of animals in each group. The collected blood was centrifuged at 4° C. at 3000 rpm for 15 minutes to obtain serum, which was then stored at −80° C. On days 0, 4, 7, 11, 14, 18, 21, 25, and 28 after the start of administration, feces was collected and lyophilized. Five % (w/v) skim milk (BD), 0.1 mg/mL soybean trypsin inhibitor (Roche Applied Science), and 2 mM phenylmethylsulfonylfluoride (Sigma) were added to PBS to prepare a solution for feces. Twenty pL of the solution for feces were added to 1 mg of dry feces. The mixture was subjected to a vortex to dissolve feces and centrifuged at 4° C. at 15,000 rpm for 10 minutes to obtain a supernatant, which was then stored at −80° C.

ELISA was performed on the obtained serum and fecal solution as follows. First, 50 µL/well of 1.0 µg/mL flagellin (InvivoGen) was added to 3 Nunc Immunoplate Maxisorb F96 Plates (Nalge Nunc) and allowed to stand overnight at 4°

C. The plates were washed with PBS, 200 μL/well of PBS containing 1% (w/v) BSA (Wako Pure Chemical Industries, Ltd.) was added, and the mixture was allowed to stand at room temperature for 2 hours. The plates were washed with TBS, and then 50 μL/well of mouse serum serially diluted with PBS was added at and further allowed to stand at room temperature for 3 hours. The plates were washed with TBS, and then 50 μL/well of Anti IgG Mouse Goat Poly-HRP 1/1000 diluted solution (R&D Systems), Anti IgA Mouse Goat Poly-HRP 1/2000 diluted solution (Santa Cruz Biotechnology), and Anti IgM Mouse Goat Poly-HRP 1/2000 diluted solution (Santa Cruz Biotechnology) were respectively added to the 3 plates and reacted at room temperature for 3 hours. The plates were washed with TBS, and then 100 μL/well of a substrate reagent OptEIA (BD) was added at and reacted at room temperature for 20 minutes with light shielding. One hundred μL/well of 1 N sulfuric acid (Wako Pure Chemical Industries, Ltd.) were added at to terminate the reaction, and absorbance at 450 nm was measured using an absorption spectrometer Ultrospec Visible Plate Reader II 96 (Amersham Biosciences).

Figure 4:
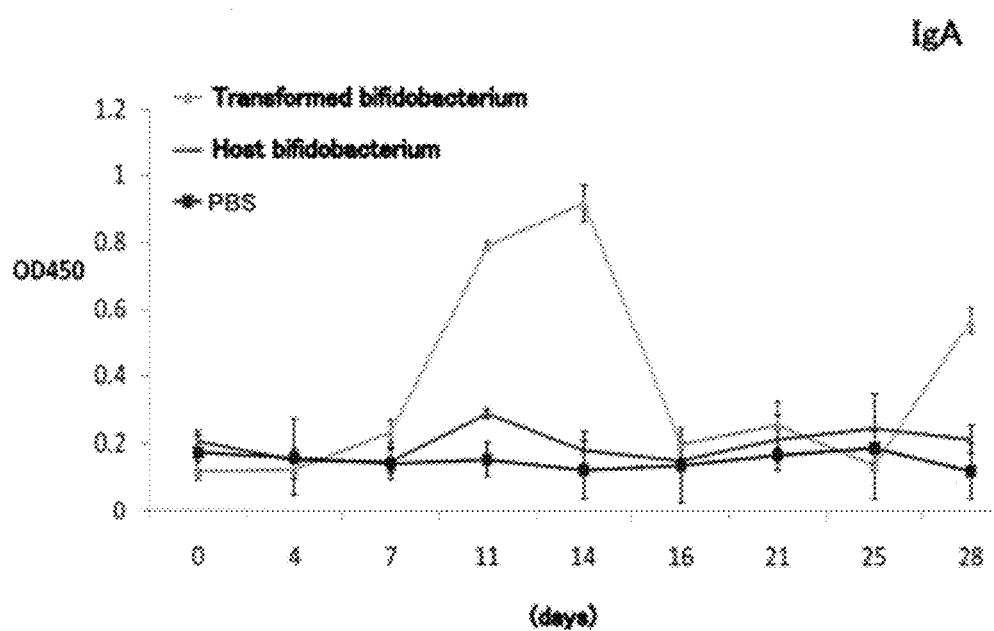
FIG. 4 is a graph showing changes with time in anti-flagellin IgA levels in feces solutions of mice orally dosed with a *bifidobacterium*.

Changes with time in anti-flagellin IgA levels in the fecal solution are shown in FIG. 4, showing that the higher the absorbance at 450 nm, the higher the IgA level. In the graph of FIG. 4, a value represents the mean value of mice in each group. The bar represents standard deviation. The anti-flagellin IgA antibody levels in feces markedly increased only in the transformed *bifidobacterium* treated group at 11 to 14 days after the start of administration.

Figure 5:
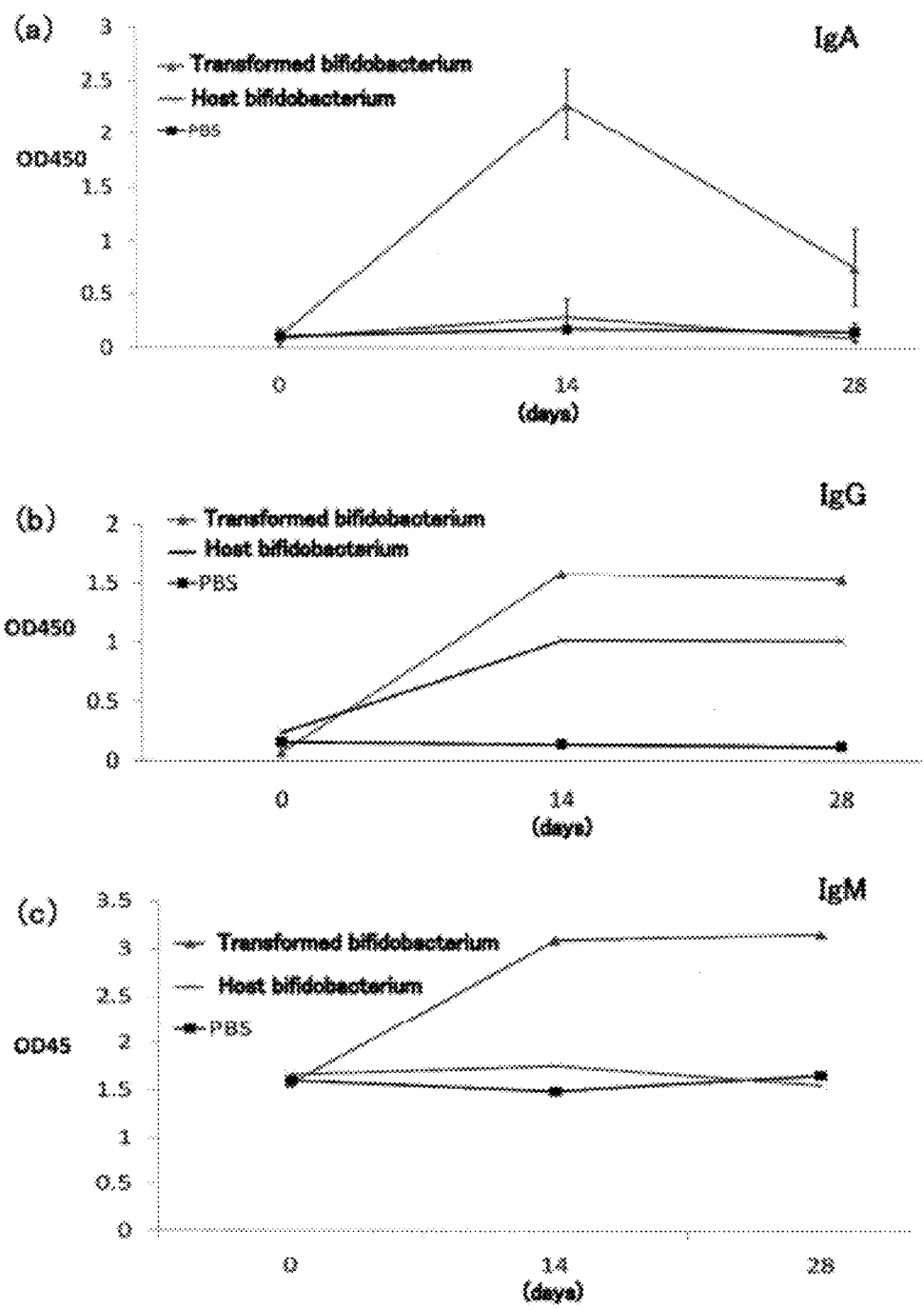
FIGS. 5(*a*), 5(*b*), and 5(*c*) are graphs showing changes with time in anti-flagellin IgA levels, anti-flagellin IgG levels, and anti-flagellin IgM levels, respectively, in serum of mice orally dosed with a *bifidobacterium*.

Changes with time in levels of various anti-flagellin antibodies in serum are shown in FIG. 5. FIG. 5(*a*) shows changes with time in anti-flagellin IgA levels, FIG. 5(*b*) shows changes with time in anti-flagellin IgG levels, and FIG. 5(*c*) shows changes with time in anti-flagellin IgM levels. The IgA levels were increased at 14 days after the start of administration as observed in the fecal solution. Both the IgG and IgM levels were increased at 14 days after the start of administration and remained high on day 28. Thus, the presence of anti-flagellin antibodies in serum by orally administering the *bifidobacterium* displaying flagellin on the surface was confirmed.

Example 6

Confirmation of Immune Response of Spleen Cells to Transformed *bifidobacterium*

The abdomens of 8- to 12-week-old female BALB/c mice were opened, and the spleens were punctured with a syringe with a 18-G needle to remove spleen cells, which were then transferred to a plate. The spleen cells were separated into single cells using a cell strainer and washed twice with sterilized PBS. The spleen cells were suspended in 0.1 M ammonium chloride solution, and this cell suspension was incubated in a dark room at 25° C. for 15 minutes. Then, the suspension was centrifuged to collect spleen cells. The collected spleen cells were suspended in an RPMI1640 medium (GIBCO) containing 10% fetal calf serum, 100 U/mL penicillin, 100 μM 2-mercaptoethanol, and 2 mM L-glutamine, and the number of cells was counted.

The spleen cells were transferred to the respective wells of a 96-well plate (Pierce Biotechnology) at 3×10$^6$ cells/well, the transformed *bifidobacterium* for administration to mice prepared in the above Example 4 was added at 50 μg/well, and the spleen cells were cultured at 25° C. for 48 hours. As a control, spleen cells were transferred to the respective wells of a 96-well plate at 3×10$^6$ cells/well and cultured at 25° C. for 48 hours without adding the transformed *bifidobacterium*. Then, the culture broth was centrifuged at 5000 g for 10 minutes to obtain a supernatant, which was then stored at −80° C.

The cytokine concentration in the supernatant was measured using commercially available ELISA kits for IFN-γ and IL-12 (Pierce Biotechnology). As a result, high levels of IFN-γ and IL-12 were detected in the supernatant from all the wells containing spleen cells cultured in the presence of the transformed *bifidobacterium*. Thus, it was confirmed that the production of IFN-γ and IL-12 was induced in mouse spleen cells by orally administering the *bifidobacterium* displaying flagellin on the surface thereof to mice.

Example 7

Mouse Infection Test Using Transformed *bifidobacterium*-1

To 8- to 12-week-old female BALB/c mice, 2.5×10$^7$ cfu/100 μL of the transformed *bifidobacterium* for administration to mice prepared in the above Example 4 was orally administered every other day for 2 weeks (test group). A *bifidobacterium* into which an empty vector (pJW241 vector) was introduced as a control (control group) and 100 μL of PBS as a negative control (negative control group) were administered to mice in the same manner as for the test group. Each group included 14 animals.

Figure 6:
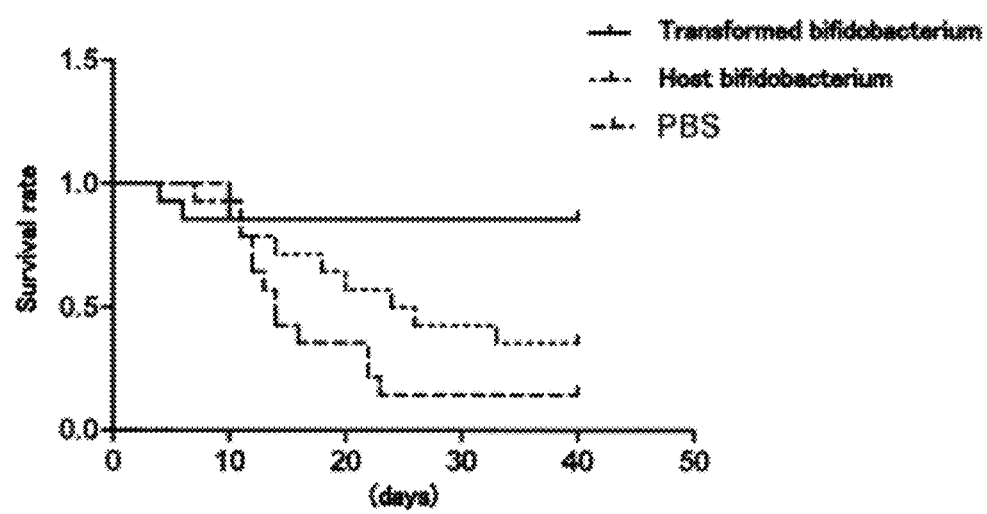
FIG. 6 is a graph showing changes with time in the survival rate of mice orally dosed with a lethal dose of *Salmonella typhimurium*.

On day 14 after the start of administration, 1.0×10$^7$ cfu, a lethal dose, of *Salmonella typhimurium* (*Salmonella enterica* subsp. *enterica* serovar *typhimurium*) ATCC14028 (purchased from Summit Pharmaceutical International Corporation) was orally administered, and then animals were visually inspected every day for 40 days. Changes with time in the survival rate of mice in each group are shown in FIG. 6. The results show that 9 of 14 animals in the control group and 12 of 14 animals in the negative control group died (the mean survival days were 14 and 25 days, respectively), but most animals survived in the test group, and only 2 of 14 animals died.

Concentrations of cytokines produced by spleen cells in the surviving animals in each group were measured using commercially available ELISA kits for IFN-γ and IL-12. The results showed that spleen cells isolated from animals in the test group produced significantly higher levels of IFN-γ and IL-12 than animals in the other groups. Thus, it was possible to effectively prevent the fatal effect of oral administration of *Salmonella typhimurium* to mice by orally administering the *bifidobacterium* displaying flagellin on the surface thereof to the mice.

Example 8

Mouse Infection Test Using Transformed *bifidobacterium*-2

At 11 days after the oral administration of *Salmonella typhimurium* in the above Example 7, the spleens were removed from animals that survived in each group, and *Salmonella typhimurium* in the spleens was detected by real time PCR analysis. First, DNA was isolated from the spleen and purified using DNeasy Blood & Tissue Kit (QIAGEN) to prepare a sample DNA solution. Genomic DNA was similarly isolated and purified from 10$^6$ to 10$^{10}$ cfu of *Salmonella Typhimurium*, which was serially diluted to prepare DNA solutions for drawing a calibration curve. Then, 12.5 μL of SYBR Green Master Mix (Applied Biosystems) containing 0.3 μmol/L each of primers ST11: 5'-gccaaccattgctaaattggcgca-3' (SEQ ID NO: 17) and ST15: 5'-ggtagaaattc-ccagcgggtactgg-3' (SEQ ID NO: 18) (Soumet C et al., Lett. Appl. Microbiol., 1999, vol. 28, pp. 113-117), and 1 μL of the sample DNA solution or the DNA solutions for drawing a calibration curve were poured into a PCR reaction tube and mixed. PCR was performed according to the protocol attached to the SYBR Green Master Mix (holding at 50° C. for 2 minutes, followed by holding at 95° C. for 10 minutes, and then repeating a cycle consisting of holding at 95° C. for 15 seconds, and holding at 60° C. for 1 minute 50 times). PCR was performed 3 times on each sample DNA solution.

As a result, *Salmonella typhimurium* DNA was not detected from the spleens of animals in the test group. On the other hand, $2.34\pm0.36\times10^{10}$ and $2.23\pm0.20\times10^{10}$ copies of *Salmonella typhimurium* DNA per milligram of the spleen DNA were detected from the spleens of animals in the control group and the negative control group, respectively. Thus, it was possible to effectively prevent *Salmonella typhimurium* infection to mice caused by oral administration by orally administering the *bifidobacterium* displaying flagellin on the surface thereof to mice.

Examples 9 to 14

Preparation of *bifidobacterium* Displaying GL-BP-FliC on the Surface Thereof and Confirmation of Surface Display of GL-BP-FliC)

Bifidobacteria transformed with the recombinant plasmid pJW245 were obtained in the same manner as in Example 1 except that *Bifidobacterium adolescentis* ATCC15703 (Example 9), *B. animalis* ATCC25527 (Example 10), *B. bifidum* ATCC11863 (Example 11), *B. breve* ATCC15700 (Example 12), *B. infantis* ATCC25962 (Example 13), or *B. pseudocatenulatum* ATCC27919 (Example 14) was used instead of *B. longum* 105-A in Example 1. The same procedure as in Example 2 was then performed, and the presence of GL-BP-FliC on the cell surface of these transformant bifidobacteria was confirmed.

INDUSTRIAL APPLICABILITY

According to the present invention, a target protein or peptide can be expressed and displayed on the cell surface of a *bifidobacterium*. For example, by displaying an antigen protein of a microorganism, a virus, a protozoon, a cancer, or the like on the surface of a *bifidobacterium*, the *bifidobacterium* can be used as an oral or nasal vaccine for transporting the antigen protein to the mucous membrane of the small intestine or the nose as a carrier and inducing an antibody reaction against the antigen displayed on the mucous membrane.

As an oral vaccine, the *bifidobacterium* can be easily taken by children and the elderly and do not cause the usual pain associated with vaccination by injection. In particular, the oral vaccine of the present invention is highly safe because bifidobacteria that have a long history of consumption are used. Furthermore, immunity is induced via the intestinal tract, which is the same route as the actual infection route, and both the humoral immunity and the cell-mediated immunity are induced.

Furthermore, enhancement of microorganism products, production of novel products, conversion of microorganisms, and the like can be achieved by displaying an enzyme on the bifidobacterial surface, and the enzyme display can be applied for biomarkers, interaction analyses, screening, and the like used in clinical practice or research.

The invention claimed is:

1. A gene for expressing a target protein or a target peptide on the cell surface of a *Bifidobacterium*, wherein an isolated gene coding for *Bifidobacterium* galacto-N-biose/lacto-N-biose (GNB/LNB) substrate-binding membrane protein and an isolated gene coding for the target protein or the target peptide are linked in this order from the 5' end side, wherein the target protein or the target peptide is displayed on the cell surface of the *Bifidobacterium*.

2. The gene of claim 1, wherein the target protein or the target peptide is a protein antigen or a peptide antigen.

3. The gene of claim 2, wherein the target protein antigen or the target peptide antigen is a *Salmonella* flagellin.

4. The gene of claim 2, wherein the target protein antigen or the target peptide antigen is M2 protein of an influenza virus.

5. The gene of claim 2, wherein an isolated gene coding for a protein having an adjuvant function is positioned between the gene coding for the GNB/LNB substrate-binding membrane protein and the gene coding for the target protein antigen or the target peptide antigen.

6. The isolated gene of claim 5, wherein the protein having the adjuvant function is a flagellin.

7. A plasmid for gene expression comprising the gene of claim 1 in an expressible form.

8. A transformed *Bifidobacterium* harboring the plasmid of claim 7 and displaying the target protein or the target peptide on its cell surface.

9. A transformed *Bifidobacterium* comprising in its genome the gene of claim 1 in an expressible form and displaying the target protein or the target peptide on its cell surface.

10. The transformed *Bifidobacterium* according to claim 7, wherein the target protein is a target protein antigen or the target peptide is a target peptide antigen.

11. The transformed *Bifidobacterium* according to claim 10, wherein the target protein antigen or the target peptide antigen is a *Salmonella* flagellin.

12. The transformed *Bifidobacterium* according to claim 10, wherein the target protein antigen or the target peptide antigen is a *Salmonella typhimurium* flagellin.

13. An oral vaccine against *Salmonella typhimurium* infection comprising the transformed *Bifidobacterium* of claim 12.

14. The transformed *Bifidobacterium* according to claim 10, wherein the target protein antigen or the target peptide antigen is M2 protein of an influenza virus.

15. The transformed *Bifidobacterium* according to claim 14, wherein a protein having an adjuvant function is further displayed on the cell surface of the transformed *Bifidobacterium*.

16. The transformed *Bifidobacterium* according to claim 15, wherein the protein having the adjuvant function is a flagellin.

17. The transformed *Bifidobacterium* according to claim 8, wherein the target protein or the target peptide is a protein antigen or a peptide antigen having an adjuvant function.

18. The transformed *Bifidobacterium* according to claim 9, wherein the target protein or the target peptide is a *Salmonella* flagellin.

19. The transformed *Bifidobacterium* according to claim 9, wherein the target protein or the target peptide is M2 protein of an influenza virus.

20. The transformed *Bifidobacterium* according to claim 9, wherein the target protein or the target peptide is a protein antigen or a peptide antigen having an adjuvant function.

21. The transformed *Bifidobacterium* according to claim 19, wherein a protein having an adjuvant function is further displayed on the cell surface of the transformed *Bifidobacterium*.

* * * * *

UNITED STATES PATENT AND TRADEMARK OFFICE
CERTIFICATE OF CORRECTION

PATENT NO. : 8,354,113 B2
APPLICATION NO. : 13/124178
DATED : January 15, 2013
INVENTOR(S) : Toshiro Shirakawa et al.

It is certified that error appears in the above-identified patent and that said Letters Patent is hereby corrected as shown below:

Claims, col 39, line 59, "10. The transformed *Bifidobacterium* according to claim 7" should read
-- "10. The transformed *Bifidobacterium* according to claim 8"

Signed and Sealed this
Twenty-third Day of April, 2013

Teresa Stanek Rea
*Acting Director of the United States Patent and Trademark Office*

SEQUENCE LISTING

<160> NUMBER OF SEQ ID NOS: 18

<210> SEQ ID NO 1
<211> LENGTH: 1317
<212> TYPE: DNA
<213> ORGANISM: Bifidobacterium longum subsp. longum JCM1217
<220> FEATURE:
<221> NAME/KEY: CDS
<222> LOCATION: (1)..(1317)
<223> OTHER INFORMATION: GL-BP

<400> SEQUENCE: 1

```
atg gta tct cgc aat aag cgc atc gtg gct gct ttt gcc gcg gta gca       48
Met Val Ser Arg Asn Lys Arg Ile Val Ala Ala Phe Ala Ala Val Ala
1               5                   10                  15 gca atg gga atg ggc ttg gcc ggt tgc ggc agc gac act gcc ggc gac       96
Ala Met Gly Met Gly Leu Ala Gly Cys Gly Ser Asp Thr Ala Gly Asp
            20                  25                  30 acg aag acc acc gat gat ggt ggc gtg gtc aac atc acc tac atg cac      144
Thr Lys Thr Thr Asp Asp Gly Gly Val Val Asn Ile Thr Tyr Met His
        35                  40                  45 cgt ctg ccg gat tcc gag ggc atg act ctg gtc aac gac atc gtt gcc      192
Arg Leu Pro Asp Ser Glu Gly Met Thr Leu Val Asn Asp Ile Val Ala
    50                  55                  60 aag tgg aat aag cag cat ccg gat att cag gtc aag gcc acc aag ttc      240
Lys Trp Asn Lys Gln His Pro Asp Ile Gln Val Lys Ala Thr Lys Phe
65                  70                  75                  80
```

-continued

| | | |
|---|---|---|
| gat ggt aag gcc tct gac atg atc aag aag ctt gag acc gac gtc aag<br>Asp Gly Lys Ala Ser Asp Met Ile Lys Lys Leu Glu Thr Asp Val Lys<br>                  85                    90                  95 | 288 |
| tcc ggc gag gct ccg gat ctg gct cag gtc ggt tac gcc gag ctg cct<br>Ser Gly Glu Ala Pro Asp Leu Ala Gln Val Gly Tyr Ala Glu Leu Pro<br>          100                  105                  110 | 336 |
| gag gtc ttc acc aag ggt ctg ctg cag gat gtg acc cag tat gcc gag<br>Glu Val Phe Thr Lys Gly Leu Leu Gln Asp Val Thr Gln Tyr Ala Glu<br>115                  120                  125 | 384 |
| cag tac aag aac gac ttc gca tcc ggc ccg tac agc ctg gtt cag gtt<br>Gln Tyr Lys Asn Asp Phe Ala Ser Gly Pro Tyr Ser Leu Val Gln Val<br>130                  135                  140 | 432 |
| ggc ggc aag gct tac ggc ctg ccg cag gac acc ggc ccg ctg gtt tac<br>Gly Gly Lys Ala Tyr Gly Leu Pro Gln Asp Thr Gly Pro Leu Val Tyr<br>145                  150                  155                  160 | 480 |
| ttc tac aac aag gct gag ttc gag aag ctc ggc atc acc gag att ccg<br>Phe Tyr Asn Lys Ala Glu Phe Glu Lys Leu Gly Ile Thr Glu Ile Pro<br>                  165                  170                  175 | 528 |
| cag acc gcc gat gag ttt atc gcc gct gcc aag acc gct gcc gcc gct<br>Gln Thr Ala Asp Glu Phe Ile Ala Ala Ala Lys Thr Ala Ala Ala Ala<br>                        180                  185                  190 | 576 |
| ggc aag tac atc atg tcc tac cag cct gat gag gcc ggc aac atg atc<br>Gly Lys Tyr Ile Met Ser Tyr Gln Pro Asp Glu Ala Gly Asn Met Ile<br>                  195                  200                  205 | 624 |
| tcc ggt ctg gct ggc gcc tcc ggt ggt tgg tac aag gtg aag ggc gac<br>Ser Gly Leu Ala Gly Ala Ser Gly Gly Trp Tyr Lys Val Lys Gly Asp<br>210                  215                  220 | 672 |
| tcc tgg gtc gtc aac acc gag acc gat ggc tcc aag gca acc gct gac<br>Ser Trp Val Val Asn Thr Glu Thr Asp Gly Ser Lys Ala Thr Ala Asp<br>225                  230                  235                  240 | 720 |
| ttc tac cag cag ctg ctc gac gcc aag gca gcc acc acc aac ccg cgt<br>Phe Tyr Gln Gln Leu Leu Asp Ala Lys Ala Ala Thr Thr Asn Pro Arg<br>                        245                  250                  255 | 768 |
| tgg gat ccg tcc ttc gat gca tcc atc aag gat ggc tcg ttg atc ggt<br>Trp Asp Pro Ser Phe Asp Ala Ser Ile Lys Asp Gly Ser Leu Ile Gly<br>                  260                  265                  270 | 816 |
| act gtg gcc gcc gct tgg gaa gcc ccg ctg ttc atg acc tcc tcc ggt<br>Thr Val Ala Ala Ala Trp Glu Ala Pro Leu Phe Met Thr Ser Ser Gly<br>          275                  280                  285 | 864 |
| ggc acc ggc tcc ggc gaa tgg cag gtc gct cag ctc ggt gac tgg ttc<br>Gly Thr Gly Ser Gly Glu Trp Gln Val Ala Gln Leu Gly Asp Trp Phe<br>290                  295                  300 | 912 |
| ggc aac gct ggc aag acc ggc cct gac ggt ggt tcc gcc gtg gcc gtg<br>Gly Asn Ala Gly Lys Thr Gly Pro Asp Gly Gly Ser Ala Val Ala Val<br>305                  310                  315                  320 | 960 |
| ctg aag aac tcc aag cac ccg aag gaa gca atg gag ttc ctg gat tgg<br>Leu Lys Asn Ser Lys His Pro Lys Glu Ala Met Glu Phe Leu Asp Trp<br>                        325                  330                  335 | 1008 |
| ttc aac acc cag gtt cct gat ctg gtt tcc cag ggc ctc gtg ccg gct<br>Phe Asn Thr Gln Val Pro Asp Leu Val Ser Gln Gly Leu Val Pro Ala<br>                    340                  345                  350 | 1056 |
| gct acc act gaa gac gct gag act cct tcc gag tgg tcc acc ttc ttc<br>Ala Thr Thr Glu Asp Ala Glu Thr Pro Ser Glu Trp Ser Thr Phe Phe<br>                  355                  360                  365 | 1104 |
| ggt ggt cag gac atc atg aag gaa ttc aag acc gct aac aac aac atg<br>Gly Gly Gln Asp Ile Met Lys Glu Phe Lys Thr Ala Asn Asn Asn Met<br>370                  375                  380 | 1152 |
| ggt gac ttc acc tac atg cct ggc ttc tcc gca gtc gcc gcc aag atg<br>Gly Asp Phe Thr Tyr Met Pro Gly Phe Ser Ala Val Ala Ala Lys Met<br>385                  390                  395                  400 | 1200 |

```
aac gaa acc gcc gcc aag gcc acc gat ggc tcc ggc aag gtt gca gac    1248
Asn Glu Thr Ala Ala Lys Ala Thr Asp Gly Ser Gly Lys Val Ala Asp
            405                 410                 415 atc ttc tcc gac gca cag acc acc tct gtg gat acg ctg aag aac ttc    1296
Ile Phe Ser Asp Ala Gln Thr Thr Ser Val Asp Thr Leu Lys Asn Phe
        420                 425                 430 ggc ctg tct gtt tcc gag tga                                        1317
Gly Leu Ser Val Ser Glu
        435

<210> SEQ ID NO 2
<211> LENGTH: 438
<212> TYPE: PRT
<213> ORGANISM: Bifidobacterium longum subsp. longum JCM1217

<400> SEQUENCE: 2
```

Met Val Ser Arg Asn Lys Arg Ile Val Ala Ala Phe Ala Ala Val Ala
1               5                   10                  15

Ala Met Gly Met Gly Leu Ala Gly Cys Gly Ser Asp Thr Ala Gly Asp
            20                  25                  30

Thr Lys Thr Thr Asp Asp Gly Gly Val Val Asn Ile Thr Tyr Met His
        35                  40                  45

Arg Leu Pro Asp Ser Glu Gly Met Thr Leu Val Asn Asp Ile Val Ala
    50                  55                  60

Lys Trp Asn Lys Gln His Pro Asp Ile Gln Val Lys Ala Thr Lys Phe
65                  70                  75                  80

Asp Gly Lys Ala Ser Asp Met Ile Lys Lys Leu Glu Thr Asp Val Lys
                85                  90                  95

Ser Gly Glu Ala Pro Asp Leu Ala Gln Val Gly Tyr Ala Glu Leu Pro
            100                 105                 110

Glu Val Phe Thr Lys Gly Leu Leu Gln Asp Val Thr Gln Tyr Ala Glu
        115                 120                 125

Gln Tyr Lys Asn Asp Phe Ala Ser Gly Pro Tyr Ser Leu Val Gln Val
    130                 135                 140

Gly Gly Lys Ala Tyr Gly Leu Pro Gln Asp Thr Gly Pro Leu Val Tyr
145                 150                 155                 160

Phe Tyr Asn Lys Ala Glu Phe Glu Lys Leu Gly Ile Thr Glu Ile Pro
                165                 170                 175

Gln Thr Ala Asp Glu Phe Ile Ala Ala Ala Lys Thr Ala Ala Ala Ala
            180                 185                 190

Gly Lys Tyr Ile Met Ser Tyr Gln Pro Asp Glu Ala Gly Asn Met Ile
        195                 200                 205

Ser Gly Leu Ala Gly Ala Ser Gly Gly Trp Tyr Lys Val Lys Gly Asp
    210                 215                 220

Ser Trp Val Val Asn Thr Glu Thr Asp Gly Ser Lys Ala Thr Ala Asp
225                 230                 235                 240

Phe Tyr Gln Gln Leu Leu Asp Ala Lys Ala Ala Thr Thr Asn Pro Arg
                245                 250                 255

Trp Asp Pro Ser Phe Asp Ala Ser Ile Lys Asp Gly Ser Leu Ile Gly
            260                 265                 270

Thr Val Ala Ala Ala Trp Glu Ala Pro Leu Phe Met Thr Ser Ser Gly
        275                 280                 285

Gly Thr Gly Ser Gly Glu Trp Gln Val Ala Gln Leu Gly Asp Trp Phe
    290                 295                 300

Gly Asn Ala Gly Lys Thr Gly Pro Asp Gly Gly Ser Ala Val Ala Val
305                 310                 315                 320

-continued

```
Leu Lys Asn Ser Lys His Pro Lys Glu Ala Met Glu Phe Leu Asp Trp
            325                 330                 335

Phe Asn Thr Gln Val Pro Asp Leu Val Ser Gln Gly Leu Val Pro Ala
        340                 345                 350

Ala Thr Thr Glu Asp Ala Glu Thr Pro Ser Glu Trp Ser Thr Phe Phe
        355                 360                 365

Gly Gly Gln Asp Ile Met Lys Glu Phe Lys Thr Ala Asn Asn Asn Met
    370                 375                 380

Gly Asp Phe Thr Tyr Met Pro Gly Phe Ser Ala Val Ala Ala Lys Met
385                 390                 395                 400

Asn Glu Thr Ala Ala Lys Ala Thr Asp Gly Ser Gly Lys Val Ala Asp
            405                 410                 415

Ile Phe Ser Asp Ala Gln Thr Thr Ser Val Asp Thr Leu Lys Asn Phe
        420                 425                 430

Gly Leu Ser Val Ser Glu
        435

<210> SEQ ID NO 3
<211> LENGTH: 1488
<212> TYPE: DNA
<213> ORGANISM: Salmonella enterica subsp. enterica serovar Typhimurium
<220> FEATURE:
<221> NAME/KEY: CDS
<222> LOCATION: (1)..(1488)
<223> OTHER INFORMATION: FliC

<400> SEQUENCE: 3 atg gca caa gtc att aat aca aac agc ctg tcg ctg ttg acc cag aat      48
Met Ala Gln Val Ile Asn Thr Asn Ser Leu Ser Leu Leu Thr Gln Asn
1               5                   10                  15 aac ctg aac aaa tcc cag tcc gct ctg ggc acc gct atc gag cgt ctg      96
Asn Leu Asn Lys Ser Gln Ser Ala Leu Gly Thr Ala Ile Glu Arg Leu
            20                  25                  30 tct tcc ggt ctg cgt atc aac agc gcg aaa gac gat gcg gca ggt cag     144
Ser Ser Gly Leu Arg Ile Asn Ser Ala Lys Asp Asp Ala Ala Gly Gln
        35                  40                  45 gcg att gct aac cgt ttt acc gcg aac atc aaa ggt ctg act cag gct     192
Ala Ile Ala Asn Arg Phe Thr Ala Asn Ile Lys Gly Leu Thr Gln Ala
    50                  55                  60 tcc cgt aac gct aac gac ggt atc tcc att gcg cag acc act gaa ggc     240
Ser Arg Asn Ala Asn Asp Gly Ile Ser Ile Ala Gln Thr Thr Glu Gly
65                  70                  75                  80 gcg ctg aac gaa atc aac aac aac ctg cag cgt gtg cgt gaa ctg gcg     288
Ala Leu Asn Glu Ile Asn Asn Asn Leu Gln Arg Val Arg Glu Leu Ala
                85                  90                  95 gtt cag tct gct aac agc acc aac tcc cag tct gac ctc gac tcc atc     336
Val Gln Ser Ala Asn Ser Thr Asn Ser Gln Ser Asp Leu Asp Ser Ile
            100                 105                 110 cag gct gaa atc acc cag cgc ctg aac gaa atc gac cgt gta tcc ggc     384
Gln Ala Glu Ile Thr Gln Arg Leu Asn Glu Ile Asp Arg Val Ser Gly
        115                 120                 125 cag act cag ttc aac ggc gtg aaa gtc ctg gcg cag gac aac acc ctg     432
Gln Thr Gln Phe Asn Gly Val Lys Val Leu Ala Gln Asp Asn Thr Leu
    130                 135                 140 acc atc cag gtt ggt gcc aac gac ggt gaa act atc gat atc gat ctg     480
Thr Ile Gln Val Gly Ala Asn Asp Gly Glu Thr Ile Asp Ile Asp Leu
145                 150                 155                 160 aag cag atc aac tct cag acc ctg ggt ctg gat acg ctg aat gtg caa     528
Lys Gln Ile Asn Ser Gln Thr Leu Gly Leu Asp Thr Leu Asn Val Gln
                165                 170                 175
```

```
caa aaa tat aag gtc agc gat acg gct gca act gtt aca gga tat gcc         576
Gln Lys Tyr Lys Val Ser Asp Thr Ala Ala Thr Val Thr Gly Tyr Ala
        180                 185                 190 gat act acg att gct tta gac aat agt act ttt aaa gcc tcg gct act         624
Asp Thr Thr Ile Ala Leu Asp Asn Ser Thr Phe Lys Ala Ser Ala Thr
    195                 200                 205 ggt ctt ggt ggt act gac cag aaa att gat ggc gat tta aaa ttt gat         672
Gly Leu Gly Gly Thr Asp Gln Lys Ile Asp Gly Asp Leu Lys Phe Asp
210                 215                 220 gat acg act gga aaa tat tac gcc aaa gtt acc gtt acg ggg gga act         720
Asp Thr Thr Gly Lys Tyr Tyr Ala Lys Val Thr Val Thr Gly Gly Thr
225                 230                 235                 240 ggt aaa gat ggc tat tat gaa gtt tcc gtt gat aag acg aac ggt gag         768
Gly Lys Asp Gly Tyr Tyr Glu Val Ser Val Asp Lys Thr Asn Gly Glu
            245                 250                 255 gtg act ctt gct ggc ggt gcg act tcc ccg ctt aca ggt gga cta cct         816
Val Thr Leu Ala Gly Gly Ala Thr Ser Pro Leu Thr Gly Gly Leu Pro
        260                 265                 270 gcg aca gca act gag gat gtg aaa aat gta caa gtt gca aat gct gat         864
Ala Thr Ala Thr Glu Asp Val Lys Asn Val Gln Val Ala Asn Ala Asp
    275                 280                 285 ttg aca gag gct aaa gcc gca ttg aca gca gca ggt gtt acc ggc aca         912
Leu Thr Glu Ala Lys Ala Ala Leu Thr Ala Ala Gly Val Thr Gly Thr
290                 295                 300 gca tct gtt gtt aag atg tct tat act gat aat aac ggt aaa act att         960
Ala Ser Val Val Lys Met Ser Tyr Thr Asp Asn Asn Gly Lys Thr Ile
305                 310                 315                 320 gat ggt ggt tta gca gtt aag gta ggc gat gat tac tat tct gca act        1008
Asp Gly Gly Leu Ala Val Lys Val Gly Asp Asp Tyr Tyr Ser Ala Thr
            325                 330                 335 caa aat aaa gat ggt tcc ata agt att aat act acg aaa tac act gca        1056
Gln Asn Lys Asp Gly Ser Ile Ser Ile Asn Thr Thr Lys Tyr Thr Ala
        340                 345                 350 gat gac ggt aca tcc aaa act gca cta aac aaa ctg ggt ggc gca gac        1104
Asp Asp Gly Thr Ser Lys Thr Ala Leu Asn Lys Leu Gly Gly Ala Asp
    355                 360                 365 ggc aaa acc gaa gtt gtt tct att ggt ggt aaa act tac gct gca agt        1152
Gly Lys Thr Glu Val Val Ser Ile Gly Gly Lys Thr Tyr Ala Ala Ser
370                 375                 380 aaa gcc gaa ggt cac aac ttt aaa gca cag cct gat ctg gcg gaa gcg        1200
Lys Ala Glu Gly His Asn Phe Lys Ala Gln Pro Asp Leu Ala Glu Ala
385                 390                 395                 400 gct gct aca acc acc gaa aac ccg ctg cag aaa att gat gct gct ttg        1248
Ala Ala Thr Thr Thr Glu Asn Pro Leu Gln Lys Ile Asp Ala Ala Leu
            405                 410                 415 gca cag gtt gac acg tta cgt tct gac ctg ggt gcg gta cag aac cgt        1296
Ala Gln Val Asp Thr Leu Arg Ser Asp Leu Gly Ala Val Gln Asn Arg
        420                 425                 430 ttc aac tcc gct att acc aac ctg ggc aac acc gta aac aac ctg act        1344
Phe Asn Ser Ala Ile Thr Asn Leu Gly Asn Thr Val Asn Asn Leu Thr
    435                 440                 445 tct gcc cgt agc cgt atc gaa gat tcc gac tac gcg acc gaa gtt tcc        1392
Ser Ala Arg Ser Arg Ile Glu Asp Ser Asp Tyr Ala Thr Glu Val Ser
450                 455                 460 aac atg tct cgc gcg cag att ctg cag cag gcc ggt acc tcc gtt ctg        1440
Asn Met Ser Arg Ala Gln Ile Leu Gln Gln Ala Gly Thr Ser Val Leu
465                 470                 475                 480 gcg cag gcg aac cag gtt ccg caa aac gtc ctc tct tta ctg cgt taa        1488
Ala Gln Ala Asn Gln Val Pro Gln Asn Val Leu Ser Leu Leu Arg
            485                 490                 495
```

```
<210> SEQ ID NO 4
<211> LENGTH: 495
<212> TYPE: PRT
<213> ORGANISM: Salmonella enterica subsp. enterica serovar Typhimurium

<400> SEQUENCE: 4

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
            85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
            165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240

Gly Lys Asp Gly Tyr Tyr Glu Val Ser Val Asp Lys Thr Asn Gly Glu
            245                 250                 255

Val Thr Leu Ala Gly Gly Ala Thr Ser Pro Leu Thr Gly Gly Leu Pro
            260                 265                 270

Ala Thr Ala Thr Glu Asp Val Lys Asn Val Gln Val Ala Asn Ala Asp
        275                 280                 285

Leu Thr Glu Ala Lys Ala Ala Leu Thr Ala Ala Gly Val Thr Gly Thr
    290                 295                 300

Ala Ser Val Val Lys Met Ser Tyr Thr Asp Asn Asn Gly Lys Thr Ile
305                 310                 315                 320

Asp Gly Gly Leu Ala Val Lys Val Gly Asp Asp Tyr Tyr Ser Ala Thr
            325                 330                 335

Gln Asn Lys Asp Gly Ser Ile Ser Ile Asn Thr Thr Lys Tyr Thr Ala
            340                 345                 350

Asp Asp Gly Thr Ser Lys Thr Ala Leu Asn Lys Leu Gly Gly Ala Asp
        355                 360                 365

Gly Lys Thr Glu Val Val Ser Ile Gly Gly Lys Thr Tyr Ala Ala Ser
    370                 375                 380
```

-continued

```
Lys Ala Glu Gly His Asn Phe Lys Ala Gln Pro Asp Leu Ala Glu Ala
385                 390                 395                 400

Ala Ala Thr Thr Thr Glu Asn Pro Leu Gln Lys Ile Asp Ala Ala Leu
                405                 410                 415

Ala Gln Val Asp Thr Leu Arg Ser Asp Leu Gly Ala Val Gln Asn Arg
            420                 425                 430

Phe Asn Ser Ala Ile Thr Asn Leu Gly Asn Thr Val Asn Asn Leu Thr
        435                 440                 445

Ser Ala Arg Ser Arg Ile Glu Asp Ser Asp Tyr Ala Thr Glu Val Ser
    450                 455                 460

Asn Met Ser Arg Ala Gln Ile Leu Gln Gln Ala Gly Thr Ser Val Leu
465                 470                 475                 480

Ala Gln Ala Asn Gln Val Pro Gln Asn Val Leu Ser Leu Leu Arg
                485                 490                 495
```

<210> SEQ ID NO 5
<211> LENGTH: 22
<212> TYPE: DNA
<213> ORGANISM: Artificial
<220> FEATURE:
<223> OTHER INFORMATION: primer glt-f

<400> SEQUENCE: 5
ggggtgctga tatattggtt tg                                          22

<210> SEQ ID NO 6
<211> LENGTH: 31
<212> TYPE: DNA
<213> ORGANISM: Artificial
<220> FEATURE:
<223> OTHER INFORMATION: primer glt-r

<400> SEQUENCE: 6
gctcgagctc ggaaacagac aggccgaagt t                                31

<210> SEQ ID NO 7
<211> LENGTH: 33
<212> TYPE: DNA
<213> ORGANISM: Artificial
<220> FEATURE:
<223> OTHER INFORMATION: primer fliC-f

<400> SEQUENCE: 7
cctcgagatg gcacaagtca ttaatacaaa cag                              33

<210> SEQ ID NO 8
<211> LENGTH: 29
<212> TYPE: DNA
<213> ORGANISM: Artificial
<220> FEATURE:
<223> OTHER INFORMATION: primer fliC-r

<400> SEQUENCE: 8
cctcgagtta acgcagtaaa gagaggacg                                   29

<210> SEQ ID NO 9
<211> LENGTH: 23
<212> TYPE: DNA
<213> ORGANISM: Artificial
<220> FEATURE:
<223> OTHER INFORMATION: primer pBLES-f

<400> SEQUENCE: 9
agggacttga tctgctcatc cag                                         23

<210> SEQ ID NO 10
<211> LENGTH: 28
<212> TYPE: DNA
<213> ORGANISM: Artificial
<220> FEATURE:
<223> OTHER INFORMATION: primer pBLES-r

<400> SEQUENCE: 10
ttcccattaa ataataaaac aaaaaaat                                    28

<210> SEQ ID NO 11
<211> LENGTH: 22
<212> TYPE: DNA
<213> ORGANISM: Artificial
<220> FEATURE:
<223> OTHER INFORMATION: primer pBLES-f3581

<400> SEQUENCE: 11
tagtttgcgc aacgttgttg cc                                          22

<210> SEQ ID NO 12
<211> LENGTH: 22
<212> TYPE: DNA
<213> ORGANISM: Artificial
<220> FEATURE:
<223> OTHER INFORMATION: primer pBLES-r93

<400> SEQUENCE: 12
gatttcatac acggtgcctg ac                                          22

<210> SEQ ID NO 13
<211> LENGTH: 22
<212> TYPE: DNA
<213> ORGANISM: Artificial
<220> FEATURE:
<223> OTHER INFORMATION: primer pMW118-f

<400> SEQUENCE: 13
atcacgaggc cctttcgtct tc                                          22

<210> SEQ ID NO 14
<211> LENGTH: 24
<212> TYPE: DNA
<213> ORGANISM: Artificial
<220> FEATURE:
<223> OTHER INFORMATION: primer pMW118-r

<400> SEQUENCE: 14
cctgttctat taggtgttac atgc                                        24

<210> SEQ ID NO 15
<211> LENGTH: 31
<212> TYPE: DNA
<213> ORGANISM: Artificial
<220> FEATURE:
<223> OTHER INFORMATION: primer GL-BP-NdeI-f

<400> SEQUENCE: 15
ccatatgaag tacgttgctt tgtaagggga g                                31

<210> SEQ ID NO 16
<211> LENGTH: 29
<212> TYPE: DNA
<213> ORGANISM: Artificial
<220> FEATURE:
<223> OTHER INFORMATION: primer FliC-NdeI-r

```
<400> SEQUENCE: 16
ccatatgtta acgcagtaaa gagaggacg                                        29

<210> SEQ ID NO 17
<211> LENGTH: 24
<212> TYPE: DNA
<213> ORGANISM: Artificial
<220> FEATURE:
<223> OTHER INFORMATION: primer ST11

<400> SEQUENCE: 17
gccaaccatt gctaaattgg cgca                                             24

<210> SEQ ID NO 18
<211> LENGTH: 25
<212> TYPE: DNA
<213> ORGANISM: Artificial
<220> FEATURE:
<223> OTHER INFORMATION: primer ST15

<400> SEQUENCE: 18
ggtagaaatt cccagcgggt actgg                                            25
```